US011154452B2

(12) United States Patent
Chase et al.

(10) Patent No.: US 11,154,452 B2
(45) Date of Patent: Oct. 26, 2021

(54) COMPRESSION GARMENT SYSTEM

(71) Applicant: Tactile Systems Technology, Inc., Minneapolis, MN (US)

(72) Inventors: Daniel G. Chase, Menomonie, WI (US); Mark R. Riley, Saint Paul, MN (US); Kristian Dior Gamble, Minneapolis, MN (US); Gregory R. Straka, Shoreview, MN (US)

(73) Assignee: Tactile Systems Technology, Inc., Minneapolis, MN (US)

( * ) Notice: Subject to any disclaimer, the term of this patent is extended or adjusted under 35 U.S.C. 154(b) by 1287 days.

(21) Appl. No.: 15/411,059

(22) Filed: Jan. 20, 2017

(65) Prior Publication Data
US 2017/0209332 A1  Jul. 27, 2017

Related U.S. Application Data

(60) Provisional application No. 62/281,706, filed on Jan. 21, 2016.

(51) Int. Cl.
*A61H 9/00* (2006.01)
*A61F 13/12* (2006.01)
(Continued)

(52) U.S. Cl.
CPC .......... *A61H 9/0078* (2013.01); *A61F 13/04* (2013.01); *A61F 13/12* (2013.01); *A61F 13/14* (2013.01);
(Continued)

(58) Field of Classification Search
CPC ........ A61H 9/00; A61H 9/005; A61H 9/0078; A61H 2201/5002; A61H 2201/0103; A61H 2201/0192; A61H 2201/16; A61H 2201/1602; A61H 2201/1604; A61H 2201/1609; A61H 2201/1614; A61H 2201/1619; A61H 2201/1623; A61H 2201/1645; A61H 2201/165; A61H 2201/1652; A61H 2201/168;
(Continued)

(56) References Cited

U.S. PATENT DOCUMENTS

| 1,309,783 A | 7/1919 | Slawin |
| 1,608,239 A | 11/1926 | Rosett |

(Continued)

FOREIGN PATENT DOCUMENTS

| EP | 2168555 A1 | 3/2010 |
| EP | 2 226 044 A2 | 9/2010 |

(Continued)

OTHER PUBLICATIONS

U.S. Appl. No. 29/576,157, filed Aug. 31, 2016, Chase et al.
(Continued)

*Primary Examiner* — Timothy A Stanis
*Assistant Examiner* — Matthew R Moon
(74) *Attorney, Agent, or Firm* — Mueting Raasch Group

(57) ABSTRACT

Compression garments and methods may include a head garment configured to be positioned around both sides of a head of a body from a posterior of the head to an anterior of the head and a torso garment. Such garment portions may include one or more controllable pressure applying regions to move lymph from the head downward to the torso.

15 Claims, 24 Drawing Sheets

(51) Int. Cl.
*A61F 13/14* (2006.01)
*A61F 13/04* (2006.01)
*A61H 1/00* (2006.01)

(52) U.S. Cl.
CPC ..... *A61H 1/008* (2013.01); *A61H 2201/0103* (2013.01); *A61H 2201/0192* (2013.01); *A61H 2201/1238* (2013.01); *A61H 2201/1604* (2013.01); *A61H 2201/165* (2013.01); *A61H 2201/1609* (2013.01); *A61H 2201/1614* (2013.01); *A61H 2201/1619* (2013.01); *A61H 2201/1623* (2013.01); *A61H 2201/5002* (2013.01); *A61H 2201/5071* (2013.01); *A61H 2201/5097* (2013.01); *A61H 2205/022* (2013.01); *A61H 2205/04* (2013.01); *A61H 2205/081* (2013.01); *A61H 2205/082* (2013.01); *A61H 2205/083* (2013.01); *A61H 2205/084* (2013.01)

(58) Field of Classification Search
CPC ........ A61H 2201/50; A61H 2201/5007; A61H 2201/5071; A61H 2201/5097; A61H 2205/02; A61H 2205/022; A61H 2205/023; A61H 2205/025; A61H 2205/04; A61H 2205/08; A61F 5/02; A61F 5/3707; A61F 13/12; A61F 13/14; A41D 1/00; A41D 13/1245; A41D 2400/322
USPC .................................. 600/148–152
See application file for complete search history.

(56) References Cited

U.S. PATENT DOCUMENTS

| | | | |
|---|---|---|---|
| 1,795,893 A | 3/1931 | Rosett | |
| D113,429 S | 2/1939 | Mehl | |
| 2,823,668 A | 2/1958 | Van Court et al. | |
| 3,094,118 A | 6/1963 | De Besme et al. | |
| 3,159,160 A | 12/1964 | Ullom | |
| 3,397,688 A | 8/1968 | Gottfried | |
| 3,606,890 A | 9/1971 | Gilbert | |
| 3,659,593 A | 5/1972 | Vail | |
| D224,282 S | 7/1972 | Candela | |
| D253,976 S | 1/1980 | Davidson | |
| 4,210,147 A | 7/1980 | Nestor et al. | |
| 4,317,239 A | 3/1982 | Bryska | |
| 4,765,338 A | 8/1988 | Turner et al. | |
| 4,787,372 A | 11/1988 | Ramseyer | |
| 4,884,295 A | 12/1989 | Cox | |
| D307,054 S | 4/1990 | Johnson, Jr. | |
| 4,920,963 A | 5/1990 | Brader | |
| 4,937,880 A | 7/1990 | Beard | |
| 4,940,045 A | 7/1990 | Cromartie | |
| D311,261 S | 10/1990 | Avey | |
| 5,014,365 A | 5/1991 | Schulz | |
| 5,031,246 A | 7/1991 | Kronenberger | |
| 5,033,461 A | 7/1991 | Young et al. | |
| 5,038,765 A | 8/1991 | Young et al. | |
| 5,039,247 A | 8/1991 | Young et al. | |
| 5,046,490 A | 9/1991 | Young et al. | |
| 5,083,553 A | 1/1992 | Stevenson et al. | |
| D331,300 S | 11/1992 | Fountain | |
| 5,188,587 A | 2/1993 | McGuire et al. | |
| 5,205,815 A | 4/1993 | Saunders | |
| 5,215,517 A | 6/1993 | Stevenson et al. | |
| 5,314,455 A | 5/1994 | Johnson, Jr. et al. | |
| 5,334,134 A | 8/1994 | Saunders | |
| 5,349,702 A | 9/1994 | Runckel | |
| 5,383,844 A | 1/1995 | Munoz et al. | |
| 5,399,150 A | 3/1995 | Saunders | |
| 5,407,420 A | 4/1995 | Bastyr et al. | |
| 5,449,379 A | 9/1995 | Hadtke | |
| 5,466,250 A | 11/1995 | Johnson, Jr. et al. | |
| 5,536,246 A | 7/1996 | Saunders | |
| 5,628,725 A | 5/1997 | Ostergard | |
| 5,697,962 A | 12/1997 | Brink et al. | |
| D389,584 S | 1/1998 | Leventhal et al. | |
| 5,733,321 A | 3/1998 | Brink | |
| 5,741,220 A | 4/1998 | Brink | |
| 5,792,082 A | 8/1998 | Yamanaka et al. | |
| 5,848,982 A | 12/1998 | Hoshino et al. | |
| 5,921,946 A | 7/1999 | Tillinghast et al. | |
| 5,928,262 A | 7/1999 | Harber | |
| 5,976,099 A | 11/1999 | Kellogg | |
| 6,030,412 A | 2/2000 | Klatz et al. | |
| 6,039,704 A | 3/2000 | Domenighini et al. | |
| 6,110,133 A | 8/2000 | Ritts | |
| 6,126,683 A | 10/2000 | Momtahemi | |
| 6,179,796 B1 | 1/2001 | Waldridge | |
| 6,338,723 B1 | 1/2002 | Carpenter et al. | |
| 6,436,064 B1 | 8/2002 | Kloecker | |
| 6,551,280 B1 | 4/2003 | Knighton et al. | |
| 6,592,535 B2 | 7/2003 | Ravikumar | |
| 6,645,165 B2 | 11/2003 | Waldridge et al. | |
| 6,860,862 B2 | 3/2005 | Waldridge et al. | |
| 6,966,884 B2 | 11/2005 | Waldridge et al. | |
| D522,179 S | 5/2006 | Wright | |
| 7,044,924 B1 | 5/2006 | Roth et al. | |
| 7,156,818 B2 | 1/2007 | Salmon et al. | |
| D538,509 S | 3/2007 | Silverman | |
| D554,225 S | 10/2007 | Peterson | |
| 7,311,687 B2 | 12/2007 | Hoffmeier et al. | |
| 7,396,345 B2 | 7/2008 | Knighton et al. | |
| D587,408 S | 2/2009 | Leonardi | |
| D596,805 S | 7/2009 | Leonardi | |
| 7,563,236 B2 | 7/2009 | Kazmierczak et al. | |
| 7,591,050 B2 | 9/2009 | Hammerslag | |
| D604,910 S | 11/2009 | Smaller | |
| 7,631,382 B2 | 12/2009 | Dibenedetto et al. | |
| 7,691,084 B2 | 4/2010 | Knighton et al. | |
| 7,698,909 B2 | 4/2010 | Hannula et al. | |
| 7,749,181 B2 | 7/2010 | Simmons et al. | |
| 7,771,376 B2 | 8/2010 | Roth et al. | |
| D624,705 S | 9/2010 | Wright | |
| 7,887,501 B2 | 2/2011 | Riordan et al. | |
| 7,947,003 B2 | 5/2011 | Bonnefin et al. | |
| 7,959,591 B2 | 6/2011 | Powers et al. | |
| 7,967,765 B2 | 6/2011 | Nathanson | |
| 8,046,937 B2 | 11/2011 | Beers et al. | |
| 8,096,964 B1 | 1/2012 | Bruehwiler et al. | |
| 8,147,438 B2 | 4/2012 | Livolsi et al. | |
| 8,226,698 B2 | 7/2012 | Edelman et al. | |
| 8,273,114 B2 | 9/2012 | Wasowski | |
| 8,381,362 B2 | 2/2013 | Hammerslag et al. | |
| 8,517,965 B2 | 8/2013 | Doty et al. | |
| 8,591,440 B2 | 11/2013 | Logue et al. | |
| D694,957 S | 12/2013 | Barker et al. | |
| 8,597,219 B2 | 12/2013 | Hargrave et al. | |
| D698,031 S | 1/2014 | Viner et al. | |
| 8,641,654 B2 | 2/2014 | Verkade et al. | |
| 8,667,613 B2 | 3/2014 | Blakely et al. | |
| D714,022 S | 9/2014 | Mong et al. | |
| D729,457 S | 5/2015 | Kim | |
| 9,027,408 B2 | 5/2015 | Toth et al. | |
| D733,361 S | 6/2015 | Welborn | |
| 9,114,257 B2 | 8/2015 | Helfer et al. | |
| D743,110 S | 11/2015 | Welborn | |
| D744,202 S | 12/2015 | Brown | |
| D750,843 S | 3/2016 | Welborn | |
| D751,211 S | 3/2016 | Moreland | |
| D751,768 S | 3/2016 | Kim | |
| 9,320,307 B2 | 4/2016 | Berns et al. | |
| D770,730 S | 11/2016 | Borovicka | |
| D777,380 S | 1/2017 | Win | |
| D791,441 S | 7/2017 | Van Sisseren | |
| 10,022,289 B2 | 7/2018 | Ajiki et al. | |
| D834,208 S | 11/2018 | Wennen et al. | |
| 2003/0032905 A1 | 2/2003 | Waldridge et al. | |
| 2003/0199922 A1 | 10/2003 | Buckman | |
| 2004/0054306 A1* | 3/2004 | Roth .............. | A61H 9/0078 601/152 |

(56) References Cited

U.S. PATENT DOCUMENTS

| | | |
|---|---|---|
| 2005/0148918 A1 | 7/2005 | Nathanson |
| 2005/0154336 A1 | 7/2005 | Kloecker et al. |
| 2006/0000478 A1 | 1/2006 | Taylor |
| 2006/0156517 A1 | 7/2006 | Hammerslag et al. |
| 2006/0200057 A1 | 9/2006 | Sterling |
| 2007/0088234 A1 | 4/2007 | Tseng |
| 2007/0161932 A1 | 7/2007 | Pick et al. |
| 2007/0169378 A1 | 7/2007 | Sodeberg et al. |
| 2009/0227914 A1* | 9/2009 | Kanaoka ............... A61H 23/04 601/84 |
| 2009/0254014 A1 | 10/2009 | Son |
| 2010/0228171 A1 | 9/2010 | Waldridge |
| 2011/0009793 A1 | 1/2011 | Lucero et al. |
| 2011/0087142 A1 | 4/2011 | Ravikumar et al. |
| 2011/0087143 A1 | 4/2011 | Bobev et al. |
| 2011/0172579 A1 | 7/2011 | Chiu et al. |
| 2011/0178447 A1 | 7/2011 | Helfer et al. |
| 2011/0257463 A1 | 10/2011 | Nour et al. |
| 2012/0004587 A1 | 1/2012 | Nickel et al. |
| 2012/0023648 A1 | 2/2012 | Dainese et al. |
| 2012/0116291 A1 | 5/2012 | Mogi |
| 2012/0150086 A1 | 6/2012 | Cohen |
| 2012/0179084 A1 | 7/2012 | Lipshaw et al. |
| 2013/0012847 A1 | 1/2013 | Lowe et al. |
| 2013/0012856 A1 | 1/2013 | Hammerslag et al. |
| 2013/0079854 A1 | 3/2013 | Wasowski |
| 2013/0197413 A1 | 8/2013 | Hoffmeier et al. |
| 2013/0211300 A1 | 8/2013 | Verkade et al. |
| 2013/0269219 A1 | 10/2013 | Burns et al. |
| 2013/0345612 A1 | 12/2013 | Bannister et al. |
| 2014/0018752 A1 | 1/2014 | Shuler |
| 2014/0033402 A1 | 2/2014 | Donnadieu et al. |
| 2014/0094726 A1* | 4/2014 | Malhi ............... A61H 9/0078 601/152 |
| 2014/0094728 A1 | 4/2014 | Soderberg et al. |
| 2014/0123449 A1 | 5/2014 | Soderberg et al. |
| 2014/0222121 A1 | 8/2014 | Spence et al. |
| 2014/0276271 A1 | 9/2014 | Stryker et al. |
| 2015/0119775 A1 | 4/2015 | Gildersleeve et al. |
| 2015/0157484 A1 | 6/2015 | Ex-Lubeskie et al. |
| 2015/0224011 A1 | 8/2015 | Scott et al. |
| 2015/0297437 A1 | 10/2015 | Neuenhahn et al. |
| 2016/0022528 A1 | 1/2016 | Wyatt et al. |
| 2016/0082319 A1 | 3/2016 | Macri et al. |
| 2016/0166464 A1 | 6/2016 | Douglas et al. |
| 2016/0213548 A1 | 7/2016 | John et al. |
| 2016/0220808 A1 | 8/2016 | Hyde et al. |
| 2017/0105893 A1 | 4/2017 | Kim et al. |
| 2017/0209332 A1 | 7/2017 | Chase et al. |
| 2017/0303607 A1 | 10/2017 | Iser et al. |

FOREIGN PATENT DOCUMENTS

| | | | |
|---|---|---|---|
| EP | 2 462 905 B1 | 11/2013 | |
| EP | 2671560 A1 | 12/2013 | |
| EP | 1 703 871 B1 | 5/2015 | |
| EP | 2 339 998 B1 | 5/2015 | |
| EP | 2 613 745 B1 | 6/2015 | |
| EP | 2 248 493 B1 | 9/2015 | |
| FR | 2 624 003 A1 | 11/1988 | |
| FR | 2731349 A1 * | 9/1996 | ........... A61H 9/0078 |
| FR | 2 939 642 A1 | 6/2010 | |
| FR | 2939642 A1 * | 6/2010 | ........... A61H 9/0078 |
| GB | 699152 | 10/1953 | |
| JP | 2009028387 A | 12/2009 | |
| JP | 2015-043790 A | 3/2015 | |
| WO | WO 03/041621 A1 | 5/2003 | |
| WO | WO 2007/014242 A1 | 2/2007 | |
| WO | WO 2008/033963 A2 | 3/2008 | |
| WO | WO-2013022589 A1 * | 2/2013 | ......... A61G 7/05784 |
| WO | WO 2014/151902 A1 | 9/2014 | |
| WO | WO 2014/159706 A2 | 10/2014 | |
| WO | WO 2015/038822 A1 | 3/2015 | |
| WO | WO 2015/050897 A1 | 4/2015 | |
| WO | WO 2015/117132 A1 | 8/2015 | |
| WO | WO 2015/200203 A1 | 12/2015 | |

OTHER PUBLICATIONS

U.S. Appl. No. 29/576,182, filed Aug. 31, 2016, Chase et al.
U.S. Appl. No. 15/284,858, filed Oct. 4, 2016, Wennen et al.
U.S. Appl. No. 15/284,870, filed Oct. 4, 2016, Wennen et al.
U.S. Appl. No. 15/284,888, filed Oct. 4, 2016, Wennen et al.
U.S. Appl. No. 15/286,378, filed Oct. 5, 2016, Chase et al.
U.S. Appl. No. 15/319,179, filed Dec. 15, 2016, Chase et al.
U.S. Appl. No. 15/411,003, filed Jan. 20, 2017, Wennen et al.
U.S. Appl. No. 29/595,538, filed Feb. 28, 2017, Chase et al.
U.S. Appl. No. 29/596,757, filed Mar. 10, 2017, Wennen et al.
[European Patent Office] Patent Application No. PCT/US2017/014249, filed Jan. 20, 2017; [International Search Report / Written Opinion] dated Apr. 4, 2017; 14 pages.
International Patent Application No. PCT/US2018/059468, filed Nov. 6, 2018; International Search Report / Written Opinion dated Mar. 14, 2019; 14 pages.

* cited by examiner

COMPRESSION GARMENT SYSTEM

This application claims the benefit of U.S. Provisional Application No. 62/281,706, filed Jan. 21, 2016, the disclosure of which is incorporated by reference herein in its entirety.

The present disclosure relates generally to the use of compression garments and compression garment systems and to methods for applying pressure to a portion of the body such as, e.g., a portion of a head, neck, and torso of a body.

Various types of compression garments are available, for example, such as for treatment of lymphedema, edema, wound healing, etc. For example, garments may include inflatable chambers or cells (or other actuatable elements) to provide therapy to patients and may be positioned about any body portion of a person or animal. Specifically, the garments may be positioned about body portions that exhibit swelling due to a build-up of lymph and that would benefit from compression therapy provided by the garments. For example, such chambers or cells may be inflatable to one or more different pressures in a variety of sequences to provide the therapy to the patient by moving lymph from one region to another. In other words, such compression garments may be placed around at least a portion of an individual's body for use in applying pressure to the body at an affected extremity. These compression garments may be donned (e.g., put on) and doffed (e.g., taken off) by patients themselves or with help from others.

SUMMARY

One exemplary compression garment system may include a head and torso garment and a controller. The head and torso garment may include a plurality of head pressure applying regions controllable to apply pressure to a plurality of portions of a head of a body and a plurality of torso pressure applying regions controllable to apply pressure to a plurality of portions of a torso of the body. The controller may be operably coupled to the head and torso garment to control pressure applied by the plurality of head pressure applying regions and the plurality of torso pressure applying regions in at least a preparation phase and a drainage phase. When in the preparation phase, the controller may be configured to apply pressure to the plurality of portions of the torso and the plurality of portions of the head using the plurality of torso pressure applying regions and the plurality of head pressure applying regions to prepare the torso of the body for lymph to be drained from the head and neck of the body. When in the drainage phase, the controller may be configured to apply pressure to the plurality of portions of the torso and the plurality of portions of the head using the plurality of torso pressure applying regions and the plurality of head pressure applying regions to move lymph at least from the head to the neck to the torso.

In one or more embodiments, the body may extend along an axis, and, when in the preparation phase, the controller may be further configured to apply pressure to the plurality of portions of the torso of the body outwardly from the axis using the plurality of torso pressure applying regions.

In one or more embodiments, the body extends along an axis, and, when in the preparation phase, the controller may be further configured to apply pressure to the plurality of portions of the head of the body outwardly from the face of the head using the plurality of head pressure applying regions after applying pressure to the plurality of torso pressure applying regions.

In one or more embodiments, the body extends along an axis, and, when in the drainage phase, the controller may be further configured to apply pressure to the plurality of portions of the head of the body outwardly from the face of the head using the plurality of head pressure applying regions and apply pressure to the plurality of portions of the torso of the body outwardly from the axis using the plurality of torso pressure applying regions after applying pressure to the plurality of head pressure applying regions.

In one or more embodiments, the body extends along an axis, the controller may be further configured to apply pressure to the plurality of portions of the torso using the plurality of torso pressure applying regions using a torso pressure application sequence, and the torso pressure application sequence may include application of increased pressure sequentially from portions of the plurality of portions of the torso closest to the axis of the body to portions of the plurality of portions of the torso furthest away from the axis of the body.

In one or more embodiments, the body extends along an axis, and the controller may be further configured to apply pressure to the plurality of portions of the torso using the plurality of torso pressure applying regions using a torso pressure application sequence. Further, the torso pressure application sequence may include application of increased pressure non-sequentially from portions of the plurality of portions of the torso closest to the axis of the body to portions of the plurality of portions of the torso furthest away from the axis of the body.

In one or more embodiments, the controller may be further configured to apply pressure to the plurality of portions of the head using the plurality of head pressure applying regions using a head pressure application sequence, and the head pressure application sequence may include application of increased pressure sequentially to portions of the plurality of portions of the head closest to the face of the head to portions of the plurality of portions of the head further away from the face of the head and closest the neck of the body.

In one or more embodiments, the controller may be further configured to apply pressure to the plurality of portions of the head using the plurality of head pressure applying regions using a head pressure application sequence, and the head pressure application sequence may include application of increased pressure non-sequentially to portions of the plurality of portions of the head closest to the face of the head to portions of the plurality of portions of the head further away from the face of the head and closest the neck of the body.

In one or more embodiments, the controller may be further configured to apply a first pressure to all but one of the plurality of portions of the head using the plurality of head pressure applying regions and apply a second pressure greater than the first pressure to one of the plurality of portions of the head using the plurality head pressure applying regions. In one or more embodiments, the first pressure may be about 0 mmHG. In one or more embodiments, the second pressure may be greater than or equal to 20 mmHG.

In one or more embodiments, the controller may be further configured to apply a first pressure to all but one of the plurality of portions of the torso using the plurality of torso pressure applying regions and apply a second pressure greater than the first pressure to one of the plurality of portions of the torso using the plurality torso pressure applying regions. In one or more embodiments, the first pressure is about 0 mmHG. In one or more embodiments, the second pressure may be greater than or equal to 40 mmHG.

One exemplary compression garment system may include a torso garment portion positionable proximate a torso of a body. The torso garment portion may define a plurality of torso pressure applying regions controllable to apply pressure to a plurality of portions of the torso. Further, the torso garment portion may further include a left torso garment portion to extend from the posterior of the torso across the left side of the torso to the anterior of the torso and a right torso garment portion to extend from the posterior torso across the right side of the torso to the anterior of the torso. The right torso garment portion may be removably couplable to the left torso garment portion proximate the anterior of the torso, and the right torso garment portion may be removably couplable to the left torso garment portion proximate the posterior of the torso. The torso garment portion may further include a posterior torso garment portion positionable proximate the posterior of the torso and coupled to the left and the right garment portions proximate a neck region of the torso, and a left wraparound portion extending from the posterior torso garment portion to extend around the left side of the torso to the anterior of the torso. Further, the left wraparound portion may be removably couplable to at least the left torso garment portion to tighten the torso garment portion about the torso of the body. The torso garment portion may further include a right wraparound portion extending from the posterior torso garment portion to extend around the right side of the torso to the anterior of the torso. The right wraparound portion may be removably couplable to at least the right torso garment portion to tighten the torso garment portion about the torso of the body.

In one or more embodiments, the each of the left and right wraparound portions may define a mitt opening configured to receive a hand of the body to move the left and right wraparound portion about the torso of the body. In one or more embodiments, the each of the left and right wraparound portions may include a tightening apparatus to tighten the torso garment portion proximate the body. The tightening apparatus may include at least one lace positioned between a first and second portion of the wraparound portion and a tightening device coupled to the at least one lace and configured to apply tension to the at least one lace to move the first portion of the wraparound portion relative to the second portion of the wraparound portion.

In one or more embodiments, the right torso garment portion may be removably couplable to the left torso garment portion proximate the posterior of the torso along a plurality of positions to define a plurality of different sizes for the torso garment portion. In one or more embodiments, the right torso garment portion may be removably couplable to the left torso garment portion proximate the anterior of the torso using a zipper.

In one or more embodiments, the exemplary garment may further include a neck garment portion coupled to the left and the right torso garment portions locatable proximate the neck of the body. The neck garment portion may define at least one neck pressure applying region controllable to apply pressure to at least one neck portion of the body, and the neck garment portion may be operably coupled to a selected torso pressure applying region of the plurality of torso pressure applying regions to apply the same amount of pressure as the selected torso pressure applying region.

In one or more embodiments, the exemplary garment may further include a head garment portion defining a plurality of head pressure applying regions controllable to apply pressure to one or more portions of a head of a body in conjunction with the torso garment. The plurality of torso pressure applying regions may include a plurality of left torso pressure applying regions and a plurality of right torso pressure applying regions different from the plurality of left torso pressure applying regions. Each of the plurality of left torso pressure applying regions may be operably coupled to a different right torso pressure applying region of the plurality of right torso pressure applying regions, and the operably coupled right and left torso pressure regions may share the same application pressure.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
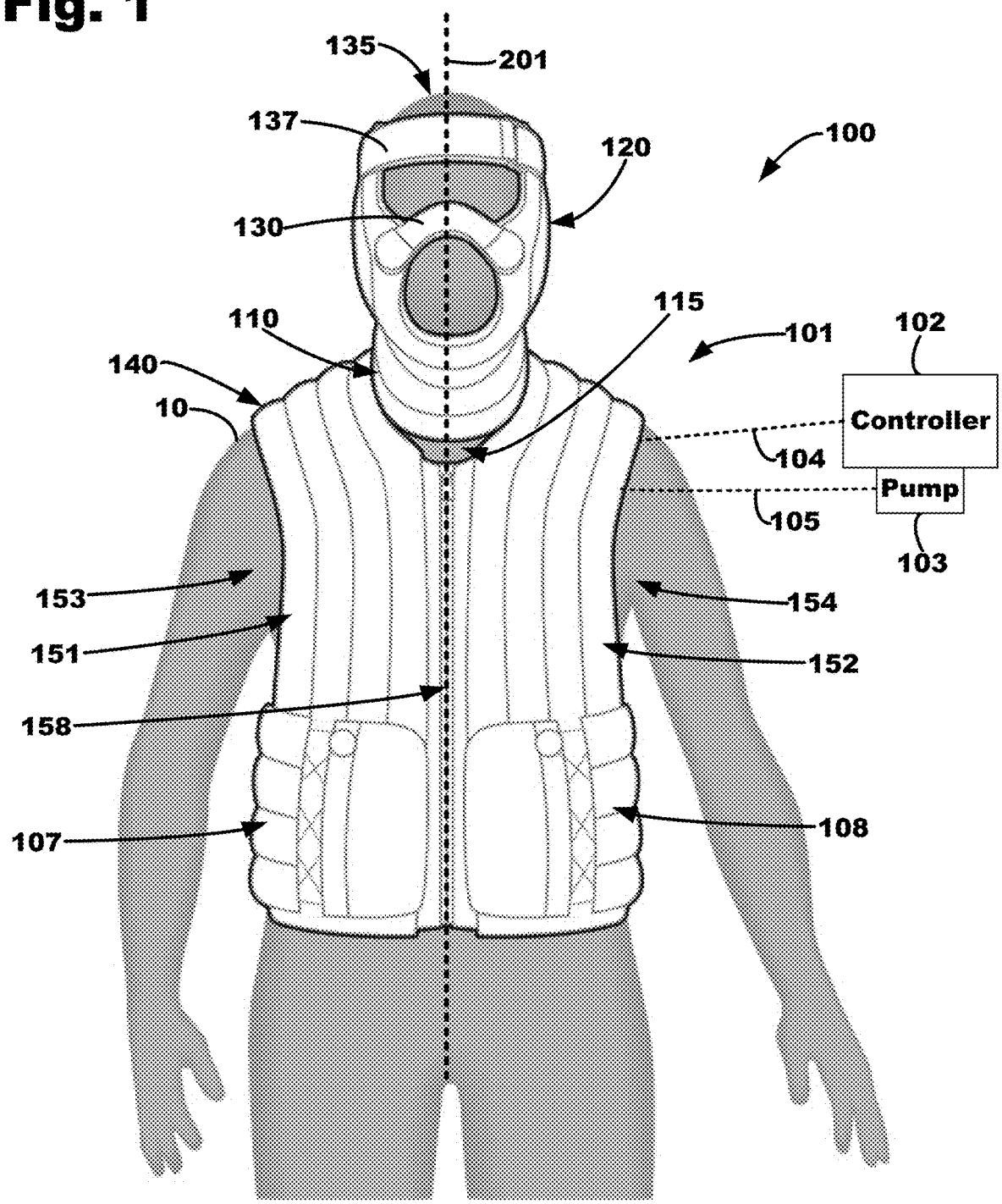
FIG. 1 is a front view of an exemplary compression system located on a body.

In the following detailed description of illustrative embodiments, reference is made to the accompanying figures of the drawing, which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, systems, structures, and methods shall be described with reference to FIGS. 1-23. It will be apparent to one skilled in the art that elements from one embodiment may be used in combination with elements of the other embodiments, and that the possible embodiments of such apparatus and systems using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garments that include garment portions that are configured to be donned on at least a portion of a body (e.g., person, animal, etc.) and configured to apply pressure to that portion of the body, compression garment systems that include compression garments and apparatus for controlling pressure applied to at least a portion of a body, and methods using such compression garments and compression garment systems (e.g., methods of donning a garment, methods of controlling pressure applied to the body, etc.)

Compression garment systems (e.g., such as compression garments described in U.S. Pat. No. 6,179,796 entitled "Lymphedema treatment system," U.S. Pat. No. 6,645,165 entitled "Lymphedema treatment system," U.S. Pat. No. 6,860,862 entitled "Lymphedema Treatment System," and U.S. Pat. No. 6,966,884 entitled "Lymphedema Treatment System," which are herein incorporated by reference and which may modify and be modified with features described herein) may be used for various reasons including therapy for people with lymphedema, animals requiring therapy, wound therapy, etc. As used herein, the term body refers to not only humans but any other animal species that may benefit from the concepts and features described herein. These compression garments may be placed around at least a portion of an individual's body and used to apply pressure to the body at an affected extremity (e.g., head, neck, arm, torso, a shoulder, etc.). Some embodiments described herein may include a compression system having a garment configured to be positioned on (e.g., wrapped around, placed adjacent, located in proximity to, etc.) at least a portion of a body (e.g., human body, arm, torso, a shoulder, head, neck, etc.). The compression garments may be donned (e.g., put on) and doffed (e.g., taken off) by individuals themselves or with help from others. The garment may also include one or more chambers (e.g., cells, compartments, sealed volumes, bladders etc.) distributed (e.g., distributed throughout, distributed in concentric patterns "radiating" away from a central point or axis, along a length, etc.) of the garment configured to receive a fluid (e.g., air) to perform compression therapy.

The compression therapy provided by the compression garment systems may help to treat lymphedema. Lymphedema is a condition of localized fluid retention and tissue swelling that may be inherited, caused by cancer treatments, caused by parasitic infections, injury, etc. For example, lymphedema of the head and neck may cause swelling around the head, neck, submandibular area, cheek, nose, eyelids, etc. Compression garments described herein covering the head and neck may be used by an affected individual to provide a therapeutic benefit. Specifically, the compression garments may be configured to manipulate lymph nodes or vessels by applying pressure to move lymph toward more beneficial locations (e.g., toward drainage areas, away from affected regions, etc.). For example, compression therapy using the systems described herein may be performed around the head and neck area to help treat lymphedema in the head and neck area by, e.g., moving lymph towards the torso.

The compression garments described herein may be configured to apply pressure to the affected regions of the body to apply compression therapy. The compression garments may include various portions that each includes controllable pressure applying regions. Each controllable pressure applying region may be configured to apply pressure to a specific portion of the body (e.g., at a specific time during therapy). The controllable pressure applying regions may work in combination with one another to help provide therapy by applying a sequence of pressures on the body that moves lymph in a desired direction (e.g., from the head towards the neck, from the neck towards the torso, etc.). Such application of a sequence of pressures on the body that moves lymph (e.g., pressure being applied to one or more portions of the head and neck, at different times during a compression therapy period) may be referred to as applying dynamic pressure to the body. The sequence of pressures may be referred to as a pressure gradients, e.g., from a distal region to a proximal region. Additionally, in some embodiments, dynamic pressure may not be applied sequentially, and instead, be applied non-sequentially as will be further described herein.

The controllable pressure applying regions of the compression garments may also apply static pressure to the body. For example, the compression garments may apply a constant pressure when a portion of the garment is positioned on the body over a therapy time period (e.g., static pressure over the therapy time period) or may apply a pressure that may be controlled to change over time during the therapy time period (e.g., dynamic pressure). In one or more embodiments, the dynamic pressure may be applied to the portion of the body through one or more chambers in the compression garment. The one or more chambers may be configured to receive fluid. Alternately, or in combination with one or more fluid receiving chambers, such pressures may be applied using one or more actuatable elements in the compression garment configured to apply pressure to the body (e.g., electrically controlled materials suitable to provide compression).

Figure 2:
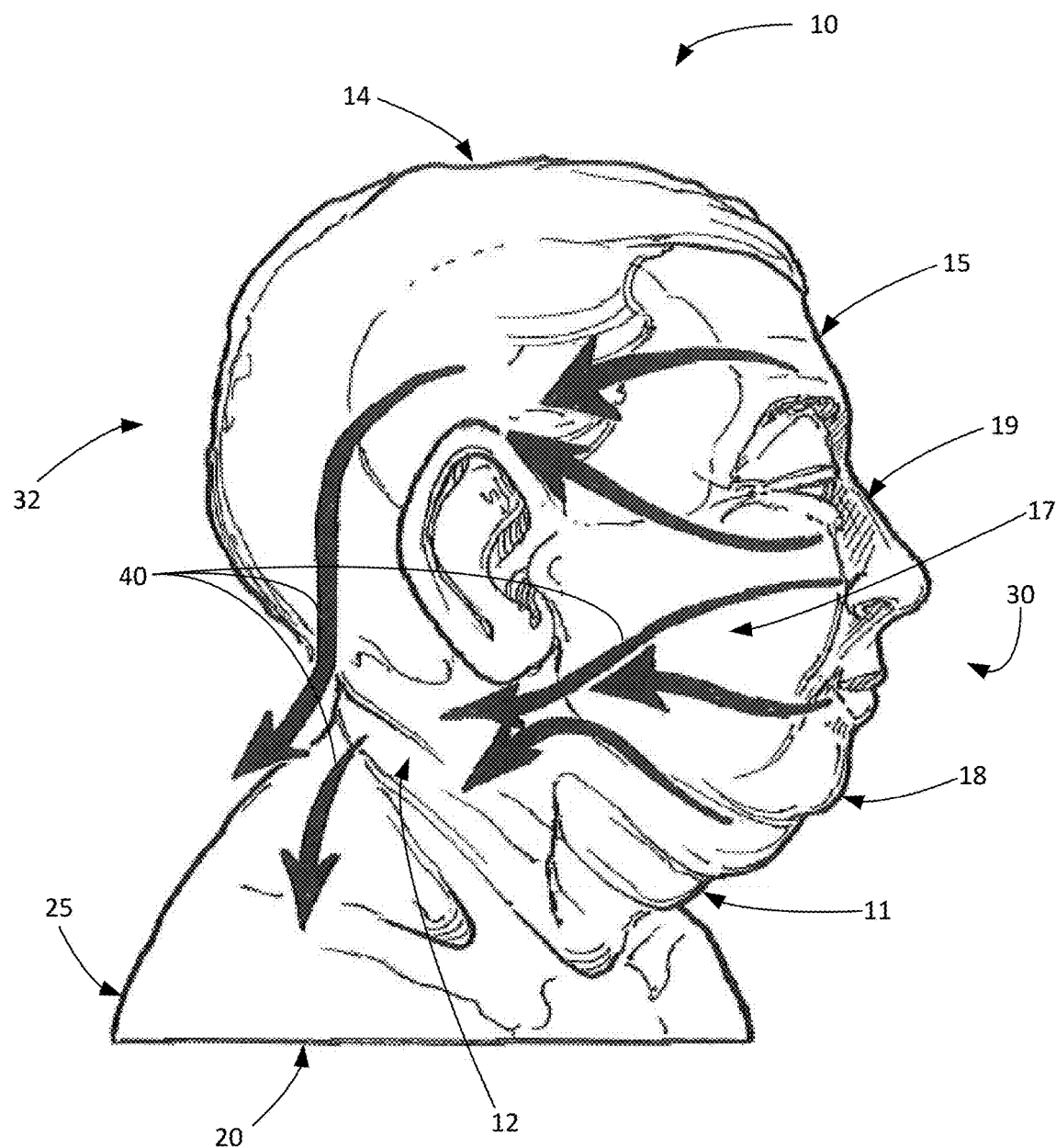
FIG. 2 is an exemplary side view of a head and a neck of a human body illustrating the directional flow of lymph through the head and neck using the exemplary compression system.
Figure 3:
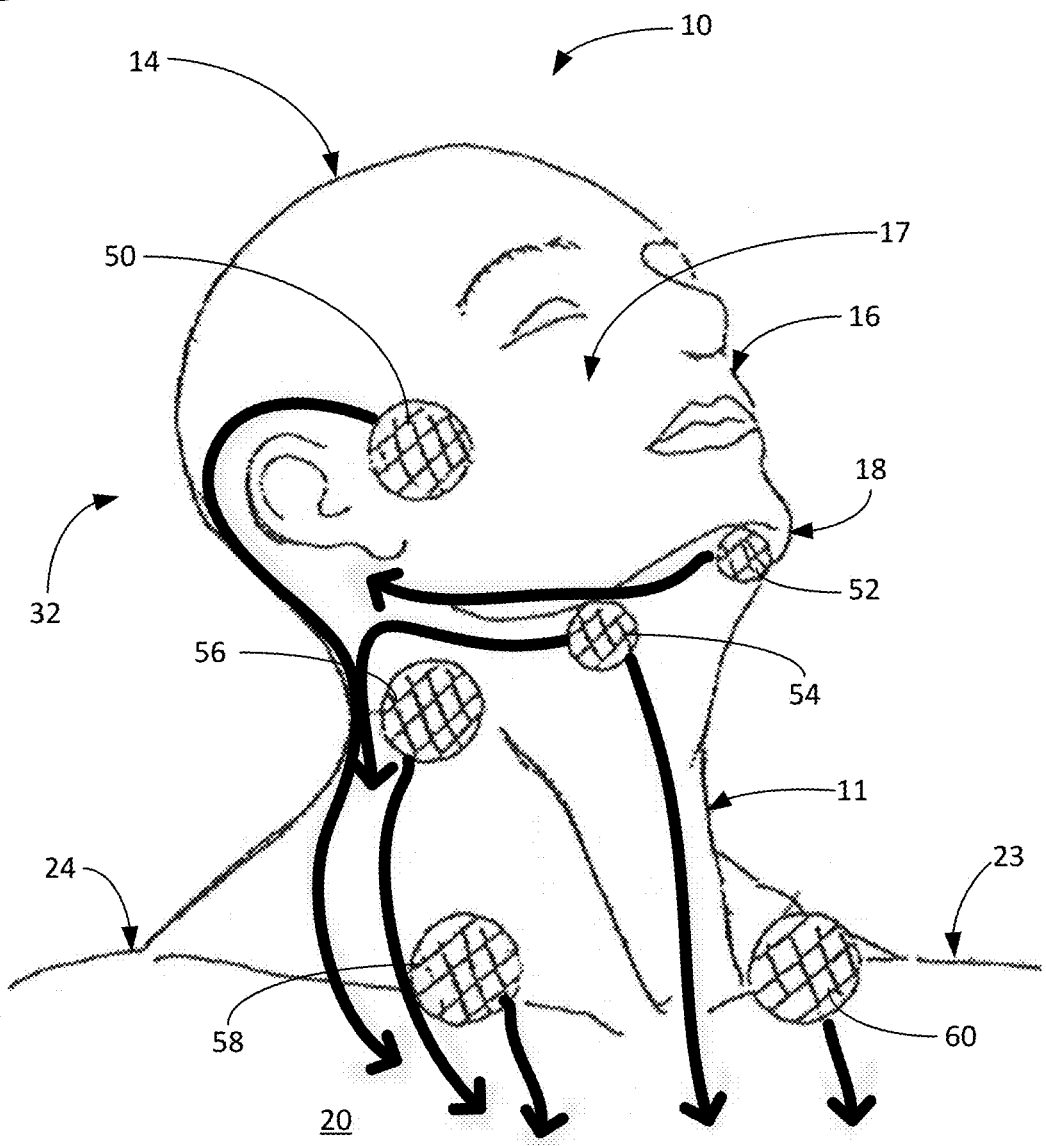
FIG. 3 is a perspective view of a head and a neck of a human body illustrating specific lymph nodes and the directional flow of lymph through the head and neck using the exemplary compression system.
Figure 4:
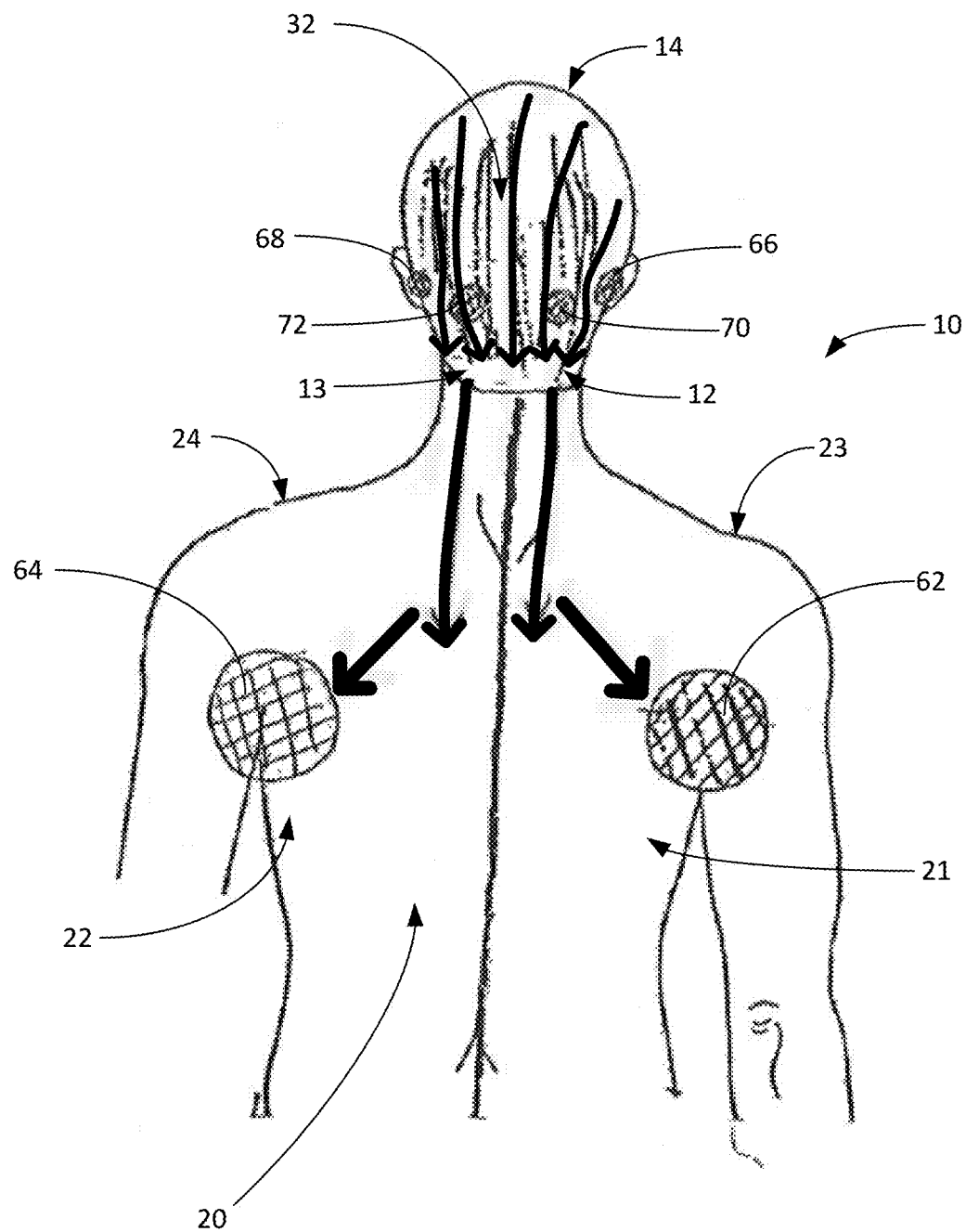
FIG. 4 is an exemplary back view of a human body illustrating specific lymph nodes and the directional flow of lymph through the body using the exemplary compression system.

An exemplary compression garment system 100 including a garment 101 (e.g., compression garment) configured to be positioned around at least a portion of a body, e.g., a human body 10, is shown in FIG. 1. The garment 101 may be positioned relative to the body in a variety of different ways (e.g., relative to a head 14, a neck 11, an anterior portion of the body 10, a posterior portion of the body 10, a forehead 15, under a chin 18, a right and left cheek 16, 17, a torso 20 as shown in FIGS. 2-4). For example, as shown in FIG. 1, the garment 101 is positioned around the head, neck, and torso of the body 10. In one or more embodiments, the garment 101 may also cover the arms, waist, legs, or any other portion of the body 10. Although as shown in FIG. 1 the garment 101 is positioned on the head, neck and torso of the body 10, the garment 101 may include only portions positioned on the head and neck of the body 10, only portions positioned on the head of the body 10, only portions positioned on the torso of the body 10, and only portions positioned on the torso and heck of the body 10.

The exemplary garment 101 may include a neck garment portion 110, a head garment portion 120, and a torso garment portion 140. Each of the neck garment portion 110, the head garment portion 120, and the torso garment portion 140 may be coupled to each other in various ways. For example, in one or more embodiments, the head garment portion 120 and the neck garment portion 110 may be coupled to one another. More specifically, the head garment portion 120 and the neck garment portion 110 may be coupled to one another at the posterior of the body 10, the anterior of the body 10, along the portion in which the head and neck garment portions 120, 110 intersect, etc.

The torso garment portion 140 may be configured to be positioned proximate the torso of the body 10. In one or more embodiments, the torso garment portion 140 may be couplable to the neck garment portion 110 (e.g., the torso garment portion 140 may be separate from the head garment portion 120 and neck garment portion 110, the torso garment portion 140 may be removably coupled to the neck garment portion 110 and/or the head garment portion 120, for example, using hook and loop fasteners, etc.). For example, the torso garment portion 140 and the neck garment portion 110 may be coupled to one another at the posterior of the body 10, the anterior of the body 10, along the portion in which the torso garment portion 140 and neck garment portion 110 intersect, etc. Still further, in one or more embodiments, the torso garment portion 140 and the neck garment portion 110 may be coupled to one another along the entire portion in which the torso garment portion 140 and neck garment portions 110 intersect (e.g., where such portions lie next to one another) or only along portions thereof (e.g., leaving openings at the coupling region for the garment to flex and adapt to the body of the user).

As shown in FIG. 1, the garment 101 may also include an open region 115 between the neck garment portion 110 and the torso garment portion 140 proximate the anterior portion of the neck and adjacent the trachea when the garment 101 is positioned on the body. The open region 115 may allow access to the airway of an individual wearing the garment 101.

The garment 101 may define, or include, pressure applying regions (e.g., as shown in FIGS. 6-7 and 18-19) located at regions of the garment 101. Each of the pressure applying regions may be controllable or configurable to apply pressure to a portion of the body. For example, the head garment portion 120 may include head pressure applying regions that are controllable or configurable to apply pressure to one or more portions of the head (e.g., to the forehead, cheeks, under the chin, posterior head), the neck garment portion 110 may include neck pressure applying regions that are controllable or configurable to apply pressure to one or more portions of the neck (e.g., posterior neck regions, side neck regions, etc.), and the torso garment portion 140 may include torso pressure applying regions controllable or configurable to apply pressure to one or more portions of the torso (e.g., torso regions under each arm, the anterior torso, the posterior torso, etc.). In one or more embodiments, the garment 101 may include an exterior material covering the pressure applying regions.

The head garment portion 120 may be configured to be donned on the head of the body 10. In other words, the head garment portion 120 may be positioned on and secured to the head of the body 10 (e.g., secured using fasteners across the nose, fasteners across the forehead, fasteners under the chin, fasteners over the top of the head, etc.). For example, such fastening apparatus may allow one garment to be adjusted for use with different size and shaped body parts. In one or more embodiments, the head garment portion 120 may be described as configured to be positioned around both sides of the head of the body 10 from the posterior of the head to the anterior of the head.

Figure 6:
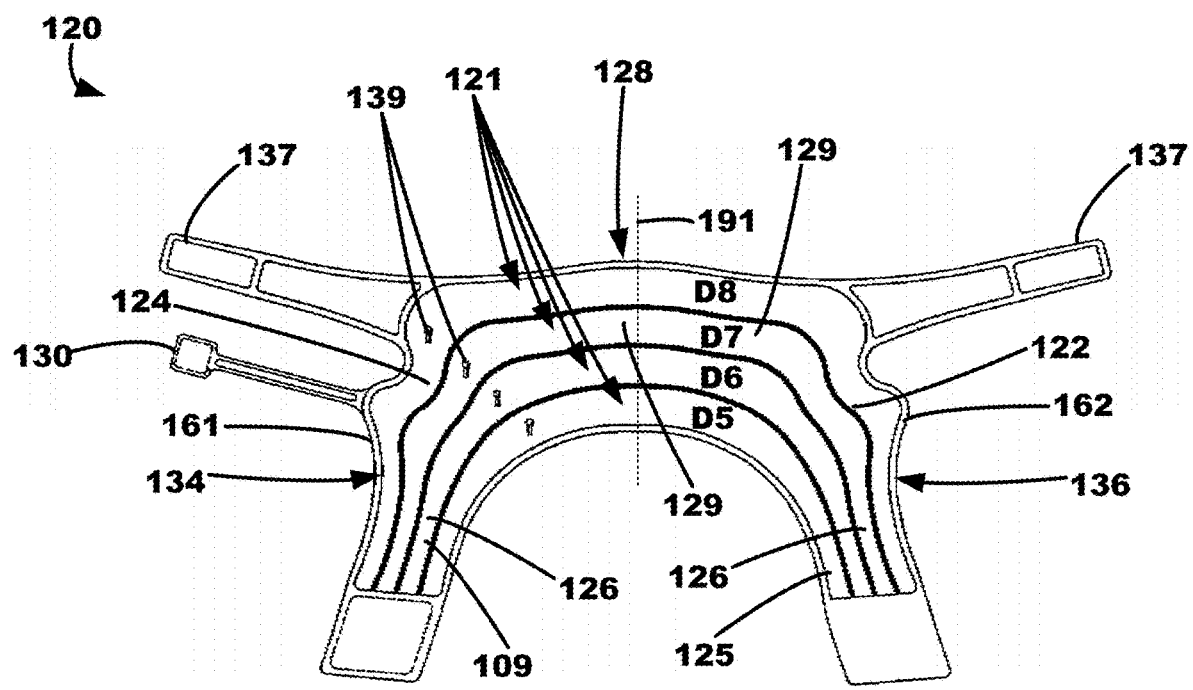
FIG. 6 is a plan view of a head garment portion of an exemplary compression garment system such as shown in FIG. 1 including one or more pressure applying regions.

As shown in the plan view of the head garment portion 120 in FIG. 6, the head garment portion 120 may include a posterior head garment portion 128, a right head garment portion 134, and a left head garment portion 136. The posterior head garment portion 128 may be positionable proximate a posterior of the head of the body 10. The right head garment portion 134 may extend from the posterior head garment portion 128 and be positionable on (e.g., wrapped around) a right side of the head from the posterior of the head to an anterior of the head. The left head garment portion 136 may extend from the posterior head garment portion 128 and be positionable on (e.g., wrapped around) a left side of the head from the posterior of the head to the anterior of the head. The posterior head garment portion 128, the right head garment portion 134, and the left head garment portion 136 (or each of such portions) may include pressure applying regions (e.g., each of the one or more head pressure applying regions for applying compression on regions of the body associated with each of such portions, one or more head pressure applying regions for applying compression on one or more regions of the body corresponding to one or more portions of the garment, etc.) that are configurable or controllable to apply pressure to the posterior of the head, the right side of the head, and the left side of the head, respectively.

The head garment portion 120 may also include a right cheek garment portion 122 and a left cheek garment portion 124. The right cheek garment portion 122 may be positionable proximate a right cheek of the head and the left cheek garment portion 124 may be positionable proximate a left cheek of the head. Each of the right and left cheek garment portions 122, 124 may include pressure applying regions (e.g., one or more cheek pressure applying regions) that may be configurable or controllable to apply pressure to a portion of cheek. The head garment portion 120 may also include a right under-chin portion 125 and a left under-chin portion 109 defining an under-chin garment portion. The under-chin garment portion may include pressure applying regions (e.g., one or more under chin pressure applying regions) that may be configurable to apply pressure to a portion under the chin (e.g., at the "waddle" area).

The head garment portion 120 may be donned on the head of the body in a variety of different ways. For example, portions of the head garment portion 120 may be attached to other portions of the head garment portion 120 using a variety of different straps or connection elements. Any suitable connection apparatus may be used for donning the head garment portion 120 or any other garment portion described herein, such as flexible or rigid connection elements, hook and loop fasteners, straps connected to the garment, additional or separate connection garment elements or straps, mating hooks, elements shaped to form to a body part (such as the bridge of the nose), etc.

These straps and connection elements may keep portions of the head garment portion 120 (e.g., surfaces associated with pressure applying regions) close to the surface of body such that the head garment portion 120 may effectively apply pressure to a particular portion of the body (e.g., the cheeks, under the chin, forehead, temples), such as, for example, when fluid is provided to chambers of pressure applying regions. In other words, the straps or connection elements may assist in preventing the head garment portion 120 from moving away from the surface of portion of the body when pressure is being applied using pressure applying regions (e.g., such as when fluid is provided to chambers of pressure applying regions) and instead, e.g., stay near the portion of the body such that pressure may be effectively applied. The different straps or connection elements keep the garment portions from moving away from the body as pressure is being applied such that even pressure applying regions (e.g., to apply pressure evenly) at edges of the garment are maintained in position during application of pressure to body regions adjacent such edges (e.g., garment edges proximate the cheeks of the head, garment edges near the chin of the head, garment edges near under the chin, garment edges near the temples of the head, etc.).

For example, the head garment portion 120 may include the under-chin garment portion including right under-chin portion 125 and left under-chin portion 109, one or more nose portions 130 and a forehead strap 137, each of which may act as restraints, straps, or connection elements to keep the head garment portion 120 in place or position. The under-chin garment portion 125 may include one or more under chin connection elements configured to connect the right cheek garment portion 122 and the left cheek garment portion 124. The one or more under chin connection elements may also be configured for use in donning the head garment portion 120 on the head of the body (e.g., tightening the head garment portion 120 into place on the head). In other words, the one or more under chin connection elements may be used to pull the right and left cheek garment portions 122, 124 closer to one another when the head garment portion 120 is positioned on the head to assist in donning the head garment portion 120 on the head.

The one or more nose, or nasal, connection elements, or portions, 130 may be positionable proximate a nasal bridge of the head and configured to connect the right cheek garment portion 122 and the left cheek garment portion 124 to, e.g., maintain the head garment portion 120 and right and left cheek garment portions 122, 124 proximate the surface of the head and cheeks. For example, the one or more nasal connection elements 130 may include a rigid portion shaped to be positioned adjacent the surface of the nasal bridge of the head (e.g., which rigid portion may be connected to the right cheek garment portion 122 and the left cheek garment portion 124 by one or more flexible portions).

The forehead strap 137 may be positionable proximate a forehead of the head. The forehead strap 137 may include one or more forehead connection elements that may be configured for use in donning the head garment portion 120 on the head. In other words, the one or more forehead connection elements may pull one portion of the head garment portion 120 closer to another portion of the head garment portion 120 to position (e.g., secure) the head garment portion 120 on the head of the body. In one or more embodiments, the head garment portion 120 may include one or more straps positioned proximate the top of the head and configured to assist in donning the head garment portion 120 on the head. For example, the forehead strap 137 may be positioned proximate the forehead of the head and may assist in donning the head garment portion 120 to the head. As shown in FIG. 1, the head garment portion 120 defines a head open region 135 proximate a top portion of the head and, e.g., between the forehead strap 137 and the posterior head garment portion 128.

One will recognize that any number of straps or connection elements may be used to connect different portions of the head garment such that the pressure applying regions thereof are properly positioned adjacent desired regions of the head and maintained in positioned as pressure is being applied either dynamically or statically. Further, one will recognize that one or more portions may be integral or separate from one another and/or the remainder of the garment.

The neck garment portion 110 as shown, e.g., in FIG. 5, may be configured to be donned on a neck of the body 10. In one or more embodiments, the neck garment portion 110 may be described as configured to be positioned around both sides of the neck from the posterior of the neck to the anterior of the neck. The neck garment portion 110 may include pressure applying regions 111 (e.g., one or more neck pressure applying regions) labeled B1, B5, or B1/B5 that may be configurable or controllable to apply pressure to a portion of the neck. As described further herein, one or more pressure applying regions of the torso garment portion 140 are also labeled B1 and B5, which, at least in some embodiments, means that the pressure applying regions 111 B1, B5 of the neck garment portion 110 are operably coupled (e.g., fluidly coupled) to the correspondingly labeled pressure applying regions of the torso garment portion 140 (e.g., coupled by tubing for fluidic transfer). In other words, pressure applying regions of different or the same garment portions that are labeled the same may be operably coupled so that such pressure applying regions inflate and deflate at the same time, share the substantially same pressure, etc.

Figure 5A:
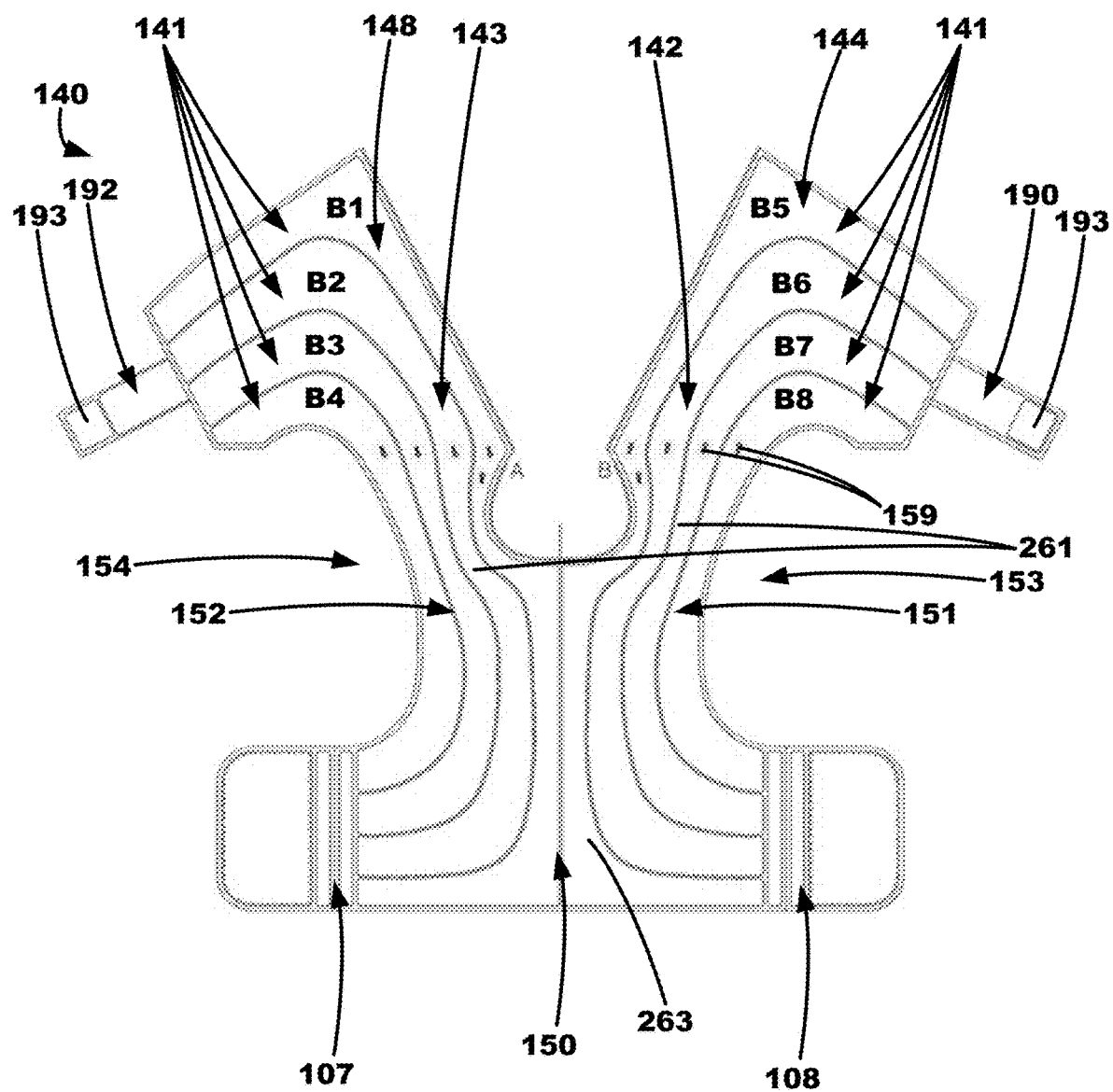
FIG. 5A is a plan view of a torso garment portion and a neck garment portion of an exemplary compression garment system such as shown in FIG. 1 including one or more pressure applying regions.
Figure 5B:
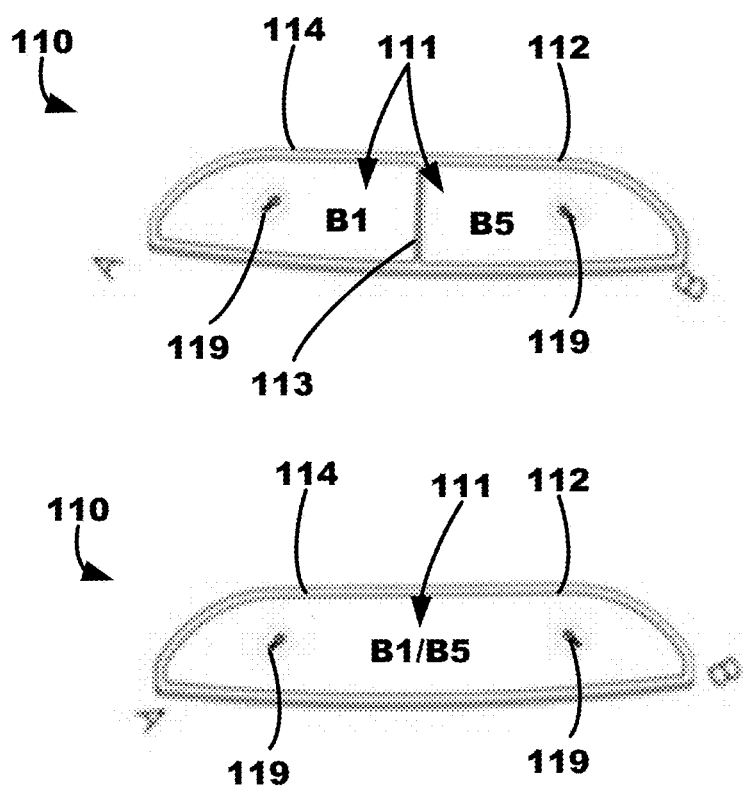
FIG. 5B is a plan view of two neck garment portions of an exemplary compression garment system such as shown in FIG. 1 including one or more pressure applying regions.

Two different neck garment portions 110 are depicted in the plan view of the neck garment portion 110 of FIG. 5B. The top, or first, neck garment portion 110 includes two separate pressure applying regions 111 and the bottom, or second, neck garment portion 110 includes a single pressure applying region 111. The neck garment portions 110 may be described as including a right neck garment portion 112, and a left neck garment portion 114. The right neck garment portion 112 may be positionable proximate a right portion or side of the neck and the left neck garment 114 portion may be positionable proximate a left portion or side of the neck. In one or more embodiments, the right neck garment portion 112 may be described as being positionable on (e.g., wrapped around) a right side of the neck from a posterior of the neck to an anterior of the neck and the left neck garment portion 114 may be described as being positionable on (e.g., wrapped around) a left side of the neck from the posterior of the neck to the anterior of the neck.

In one or more embodiments such as the top, or first, neck garment portion 110, the right neck garment portion 112 is separate from the left neck garment portion 114 (e.g., one portion may include pressure applying regions 111 separate from those in the other portion). In other embodiments such as the bottom, or second, neck garment portion 110, the right and left neck garment portions 112, 114 may be described as being "one piece" (e.g., include the same pressure applying region 111). Further, each of the right and left neck garment portions 112, 114 may be configurable or controllable to apply pressure to the right and left sides of the neck, respectively. For example, the pressure applying regions of left and right neck garment portions 112, 114 may be controllable or configurable to apply pressure alternately between each of the left and right neck garment portions 112, 114, or simultaneously. In the first or top embodiment, the one or more neck pressure applying regions 111 of the first and second neck garment portions may be separated by a divider 113. In other words, the divider 113 separates pressure applied by the one or more neck pressure applying regions 111 of the right neck garment portion 112 from the one or more neck pressure applying regions 111 of the left neck garment portion 114.

In one or more embodiments, at least a portion of the one or more neck pressure applying regions 111 may be described as defining an arcuate shape. Further, the one or more neck pressure applying regions 111 may be controllable (e.g., using controller 102 as shown in FIG. 1) to apply pressure to a portion of the neck when the neck garment portion 110 is positioned on the neck.

In one or more embodiments, each of the one or more neck pressure applying regions 111 may be configured such that the neck pressure applying regions 111 may be controlled to apply pressure to a portion of the neck. For example, the one or more neck pressure applying regions 111 may include fluid chambers or cells, pneumatic pressure applying regions, actuatable elements applying pressure to regions, hydraulic pressure applying regions, etc. Specifically, the one or more neck pressure applying regions 111 may include one or more chambers configured to receive fluid.

For example, in one or more embodiments, the one or more neck pressure applying regions 111 may be configured to apply pressure to a portion of the head using the one or more chambers through the control of fluid provided thereto, e.g., fluid flow, air flow, etc. (e.g., such as with use of pump 103 shown in FIG. 1, under control of controller 102 with use of a sensor feedback system). For example, the neck garment portion 110 may include one or more neck garment ports 119 through which fluid may be provided to the one or more chambers. In one or more embodiments, the neck garment portion 110 may include two neck garment ports 119, one in each of the right and left neck garment portions 112, 114 (e.g., such as for use in alternating application of pressure between the right and left sides of the neck).

Further, in one or more embodiments, the neck pressure applying regions 111 may include one or more neck actuatable elements (e.g., non-fluid receiving regions) configured to apply pressure to a portion of the neck (e.g., an electrical signal may be used to actuate an element within the garment, such as electrically actuatable fibers in the garment, such that the compartment including such fibers applies a pressure to a portion of the body). In one or more embodiments, the one or more neck pressure applying regions 111 may include both one or more chambers configured to receive fluid and one or more neck actuatable elements.

Any number of pressure applying regions 111 may be configured in the neck garment portion 110 such that they may be controlled to move lymph as described, for example, with reference to FIGS. 2-4. For example, as shown in FIG. 5B, one or two pressure applying regions 111 may be implemented. However, such pressure applying regions 111 may include any number of different and separate chambers along the wrappable length of the neck garment portion 110 and controllable to produce desired lymph movement (e.g., multiple chambers along the length, parallel chambers along the width, etc.).

The torso garment portion 140 may be described as configured to be positioned around both sides of the torso from the posterior of the torso to the anterior of the torso of the body 10. The torso garment portion 140 may include pressure applying regions (e.g., one or more torso pressure applying regions) configurable or controllable to apply pressure to one or more portions of the torso. In one or more embodiments, the torso garment portion 140 may be coupled to the neck garment portion 110 and/or the head garment portion 120. For example, as shown in the plan view of FIGS. 5A-5B, the ends of the neck garment portions 110 are labeled "A" and "B" which correspond to the "A" and B" labels of the neck region of the torso garment portion 140. As such, the neck garment portions 110 may be coupled to the torso garment portion 140 from label "A" to label "B." Further, upon coupling, it may be described that the neck garment portion 110 resembles, or may be referred to, as a "collar" of the torso garment portion 140. Still further, as will be described further herein, one or more pressure applying regions of the torso garment portion 140 may correspond to the one or more pressure applying regions of the neck garment portion 110 (e.g., one or more pressure applying regions of the torso garment portion may apply the same amount of pressure at the same time as one or more pressure applying regions of the neck garment portion).

Further, in one or more embodiments, the neck garment portion 110 may be coupled between at least a portion of the head garment portion 120 and at least a portion of the torso garment portion 140. In yet other embodiments, the torso garment portion 140 may not be coupled to either the head garment portion 120 or the neck garment portion 110.

The torso garment portion 140 may include a posterior torso garment portion 150, a right torso garment portion 151, and a left torso garment portion 152. The posterior torso garment portion 150 may be positionable proximate a posterior of the torso of the body, the right torso garment portion 151 may extend from the posterior torso garment portion 150 and be positionable to the anterior of the torso, and the left torso garment portion 152 may extend from the posterior torso garment portion 150 and be positionable to the anterior of the torso. In one or more embodiments, the right torso garment portion 151 may define a right arm opening 153 proximate a right arm of the body such that the right arm may extend outward from the garment 101 and the left torso garment portion 152 may define a left arm opening 154 proximate a left arm of the body such that the left arm may extend outward from the garment 101.

The right and left torso garment portions 151, 152 may be coupled to each other after donning the torso garment portion 140 on the torso of the body to attach (e.g., secure) the torso garment portion 140 to the torso. The right torso garment portion 151 may be coupled to the left torso garment portion 152 in any suitable manner. For example, the right and/or left torso garment portions 151, 152 may include fastening apparatus to, e.g., fasten or couple a region of the right torso garment portion 151 to a portion of the left torso garment portion 152. Although the right torso garment portion 151 is coupled to the left torso garment portion 152 using a zipper 158 as shown, any fastening apparatus may be used such as, e.g., hook and loop fasteners, draw strings, buttons, etc. Further, the right torso garment portion 151 may be coupled to the left torso garment portion 152 on the anterior side and the posterior side as will be described further herein with respect to FIGS. 7 & 9.

Additionally, the torso garment portion 140 may further include a left wraparound portion 107 and a right wraparound portion 108, which may be configured to further couple, or secure, the torso garment portion 140 about the torso of the body 10. More specifically, it may be described that the left and right wraparound portions 107, 108 may be configured to "tighten" the torso garment portion 140 about the torso of the body 10, which may be described further herein with respect to FIGS. 10-12.

The compression garment system 100 may also include a controller 102 or control apparatus configured to control the pressure applied to the portion of the body by each of the pressure applying regions of the garment 101. For example, the controller 102 may control the pressure applied to the portion of the body by each of the pressure applying regions independent from one another or at the same time. Further, for example, the pressure applying regions may be controlled in groups or combinations. In one or more embodiments, the controller 102 may be configured to control the pressure applying regions in a variety of different sequences (e.g., applying pressure in a predetermined manner) that may be, e.g., suitable for carrying out lymphedema therapy.

Further, the controller 102 may control the pressure based on one or more pressures measured by one or more pressure sensors associated with the garment 101 (e.g., sensors provided in the garment 101 proximate the pressure applying regions). One or more compression garments that may be modified with features (e.g., sensors) described herein may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference.

In one or more embodiments, a control apparatus or controller 102 (e.g., one or more processors employing one or more programs or routines carrying out one or more methods or processes and implemented with one or more types of memory) may be configured to control the system and/or one or more elements thereof (e.g., providing compression therapy by the one or more pressure applying regions, etc.). In one or more embodiments, the control apparatus may be configured to control the compression system using wired and/or wireless technology.

The methods and/or logic and/or configurations described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices (e.g., within the system, outside of the system, or a combination of both) to support the various operations and functions described in this disclosure. In addition, any of the described components may be implemented together or separately as discrete but interoperable logic devices. Description of different features is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

Figure 23A:
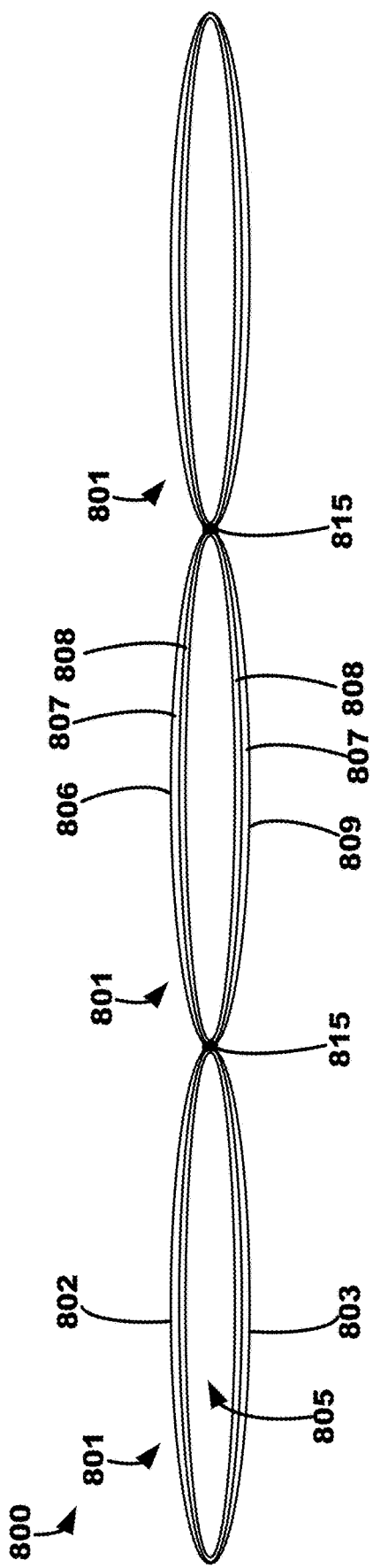
FIG. 23A is a cross-sectional view of one or more chambers or cells (e.g., inflatable chambers or cells) of an exemplary compression garment that may be used with one of the exemplary garment portions such as shown in FIGS. 1 and 5-19.

Further, the compression garment system 100 may include a pump 103 that may be controlled by the controller 102 to provide a fluid to/from the one or more chambers (e.g. one or more chambers 806 as shown in FIG. 23A) of each of the pressure applying regions, e.g., a fluid such as a liquid or gas in the chambers, so as to apply a compression therapy when the compression garment 101 includes one or more fluid filled chambers. For example, the pump 103 may be connected to one or more of the plurality of chambers corresponding to the plurality of pressure applying regions by a plurality of lines or tubing 105 so as to provide flow of fluid thereto or removal of fluid therefrom.

Further, in one or more embodiments, as shown in FIG. 1, the controller 102 may be connected to one or more components of the compression garment system via one or more electrical lines and/or wirelessly, as represented generally by dashed lines 104. For example, controller 102 may be connected to communicate and control the pressure applying regions (e.g., such as electrically actuatable pressure applying regions of the garment configured to apply pressure to the body) either with use of physical electrical connections and/or wirelessly.

The controllable pressure applying regions of the garment 101 under control of controller 102 allows the system 100 to provide compression therapy to an individual (e.g., a patient) wearing the garment 101 such that lymph flows throughout the body 10 in desired directions, e.g., such as directions 40 as shown in FIGS. 2-4. In other words, by controlling the pressure applying regions in a variety of different sequences (e.g., applying pressure in a predetermined manner), for example, lymph may flow generally from the head 14 of the body 10 towards the neck 11 of the body 10. For example, the lymph may be controlled to flow from an anterior 30 of the head 14 towards a posterior 32 of the head 14 and downwards towards the neck 11. Specifically, for example, the lymph may flow from the forehead 15, the nasal bridge 19, and under the chin 18 towards the right cheek 17 and downwards towards the neck 11 (e.g., right side of neck 12) and the posterior 25 of the torso 20. This direction 40 of lymph may provide relief to an individual by moving excess lymph from the head 14, and ultimately, moving such lymph towards the torso 20 (e.g., trunk, shoulders, chest, back, waist, etc.).

The various nodes located in the head 14 and neck 11 of the body 10 are shown in FIG. 3. For example, the submental lymph nodes 52 are located the under chin 18 of the head 14 and the parotid lymph nodes 50 are located proximate the right cheek 17 and the left cheek 16 (parotid lymph nodes of left cheek 16 not shown in FIG. 3). The accumulation of lymph may occur near the parotid lymph nodes 50 and the submental lymph nodes 52 and may be pushed during compression therapy by the compression garment donned on the body 10 towards the posterior 32 of the head 14 as illustrated by directional arrows 40 (e.g., by controlling the pressure applying regions proximate at least the cheeks and under the chin in a predetermined manner). With continued compression therapy (e.g., by controlling the pressure applying regions proximate at least the sides of the head and the posterior of the head), the lymph then moves towards the submandibular lymph nodes 54 and superficial and deep cervical lymph nodes 56 located proximate the neck 11. The compression therapy is then configured (e.g., by controlling the pressure applying regions proximate at least the neck in a predetermined manner) to move lymph towards the right infra and supra clavicular lymph nodes 58 and the left infra and supra clavicular lymph nodes 60, which are located at the base of the neck 11 and proximate the right shoulder 24 and the left shoulder 23, respectively, and downwards towards the torso 20.

Various nodes located in the posterior 32 of the head 14 and the torso 20 are shown in FIG. 4. During compression therapy using a compression garment (e.g., by controlling the pressure applying regions of the head garment 120 and neck garment 110 in a predetermined manner), lymph may travel downward along the posterior 32 of the body 10 from the head 14 towards the torso 20. For example, lymph may travel from the top of the head 14 towards the right retroauricular lymph nodes 66 and the right occipital lymph nodes 70 located proximate the right side 12 of the neck 11 and towards the left retroauricular lymph nodes 68 and the left occipital lymph nodes 72 located proximate the left side 13 of the neck 11. The compression therapy (e.g., by controlling the pressure applying regions of the garment 101 in a predetermined manner) may then move the lymph further downwards from the head 14 and past the right and left shoulders 23, 24 and towards the torso 20. Specifically, the lymph may move towards the right axillary nodes 62 located proximate the right under arm region 21 and the left axillary nodes 64 located proximate the left under arm region 22.

A plan view of the exemplary head garment portion 120 including one or more head pressure applying regions 121 labeled D8, D7, D6, & D5 is shown in FIG. 6. In one or more embodiments, it may be described that at least a portion of the one or more head pressure applying regions 121 may define an arcuate shape. The one or more head pressure applying regions 121 may be controllable (e.g., using controller 102 as shown in FIG. 1) to apply pressure to a portion of the head when the head garment portion 120 is positioned on the head. Further, the one or more head pressure applying regions 121 may be located in various locations within the head garment portion 120 to apply pressure to a variety of different locations on the head. For example, as described herein, the head garment portion 120 may include the right head garment portion 134 positionable proximate a right side of the head and the left head garment portion 136 positionable proximate a left side of the head. The one or more head pressure applying regions 121 associated with the right and left head garment portions 134, 136 may be controllable to apply pressure to the right and left sides of the head, respectively. In one or more embodiments, the pressure applying regions 121 may be split into two along dotted line 191 such that, e.g., each pressure applying region D8, D7, D6, & D5 may include a left and a right pressure applying region (e.g., which may be operably coupled such that the left and the right pressure applying region of one of D8, D7, D6, & D5 apply the same amount of pressure at the same time).

In one or more embodiments, each of the one or more head pressure applying regions 121 may be configured in any suitable manner such that the regions 121 may be controlled to apply pressure to a portion of the head. For example, the one or more head pressure applying regions 121 may include fluid chambers or cells, pneumatic pressure applying regions, actuatable elements applying pressure to regions, hydraulic pressure applying regions, etc. Specifically, the one or more head pressure applying regions 121 as well as the other pressure applying regions of the other garment portions shown therein include one or more chambers configured to receive fluid (e.g., air, liquid, etc.).

In one or more embodiments, the one or more head pressure applying regions 121 may be configured to apply pressure to a portion of the head using the one or more chambers through the control of fluid provided thereto, e.g., fluid flow, air flow, etc. For example, the head garment portion 120 may include one or more head garment ports 139 through which fluid may be provided to the one or more chambers (e.g., such as with use of pump 103 shown in FIG. 1, under control of controller 102 with use of a sensor feedback system). Further, in one or more embodiments, the one or more head pressure applying regions 121 may include one or more head actuatable elements (e.g., non-fluid receiving regions) configured to apply pressure to a portion of the head (e.g., an electrical signal may be used to actuate an element within the garment, such as electrically actuatable fibers in the garment, such that the region including such fibers applies a pressure to a portion of the body). In one or more embodiments, the one or more head pressure applying regions 121 may include both one or more chambers configured to receive fluid and one or more head actuatable elements, both of which may be configured to apply pressure to a portion of the head.

Furthermore, as described herein, the head garment portion 120 may include a right cheek garment portion 122 and a left cheek garment portion 124, each of which may include one or more cheek pressure applying regions (e.g., each of the garment portions may include a portion of a pressure applying region 121 shared with other garment portions, for example, the same pressure applying region 121 may be used to apply compression at locations of the body associated with the right cheek and left cheek, and even the posterior garment portion). Each of the one or more cheek pressure applying regions may be controllable to apply pressure to a portion of cheek to assist in moving lymph therefrom. Each of the right cheek garment portion and the left cheek garment portion 122, 124 extend within the right and left head garment portions 134, 136, respectively and terminate along right cheek and left cheek garment edges (e.g., portions of such edges being located near the nasal bridge of the head; which portions may be coupled together by one or more nose portions 130).

Similarly, as described herein, the head garment portion 120 may include the under-chin garment portion, which includes a right under-chin portion 125 and a left under-chin portion 109 that is configurable to apply pressure to a portion under the chin (e.g., a "waddle" area). For example, the under chin garment portion 125 may include one or more under chin pressure applying regions 126. Each of the one or more under chin pressure applying regions 126 may be controllable to apply pressure to a portion under the chin to assist in moving lymph therefrom.

Also, as described herein, the head garment portion 120 may include the posterior head garment portion 128. The posterior head garment portion 128 may include one or more posterior head pressure applying regions 129. Each of the one or more posterior head pressure applying regions 129 may be controllable to apply pressure to a portion of the posterior of the head to move lymph therefrom (e.g., downward toward the torso).

Any number of pressure applying regions 121 may be configured in the head garment portion 120 such that they may be controlled to move lymph as described, for example, with reference to FIGS. 2-4. For example, as shown in FIG. 6, four head pressure applying regions 121 are implemented. However, any number of head pressure applying regions 121 may be implemented such as, e.g., two head pressure applying regions 121, three head pressure applying regions 121, five head pressure applying regions 121, six head pressure applying regions 121, etc. Each of the four pressure applying regions 121 extend along the entire length of the head garment portion 120 positionable about the head of a user (e.g., from the front right side of the head around the posterior of the head and towards the front left side of the head). For example, each of the head pressure applying regions 121 extend within the under-chin garment portion 125, the right and left cheek garment portions 122, 124, and the posterior head garment portion 128 (e.g., which may be beneficial in application of pressure in a downward and rearward manner on the head). In other words, the under-chin garment portion 125, the right and left cheek garment portions 122, 124, and the posterior head garment portion 128 may be integral with each other such that head pressure applying regions 121 may span across one or more specific portions. For example, application of pressure in the outer head pressure applying region 121 (e.g., next to edges 161, 162), followed by application of pressure by more inward lying pressure applying regions, may produce desired lymph movement.

In one or more embodiments, the head pressure applying regions 121 may be positioned such that pressure may be applied in a progression from the front of the right and left cheeks (e.g., at the anterior, or front, of the head, proximate the edges of the face, the nose, etc.) towards the posterior, or backside, of the head and the neck. For example, pressure may be applied to a region proximate the right and left cheek garment portions 122, 124 at the anterior of the head, then proximate a middle of the cheeks at the right and left cheek garment portions 122, 124, and then proximate a portion of the cheeks closer to the posterior of the head at the right and left cheek garment portions 122, 124. In one or more embodiments, as pressure is being applied at the right and left cheek garment portions 122, 124 from the anterior of the head towards the posterior of the head, pressure may also be applied at the posterior head garment portion 128 from the top of the head towards the neck. In one or more embodiments, this may occur due to the continuation of the four head pressure applying regions 121 (e.g., as shown in FIG. 6) extending (e.g., along the length of the garment) between the right and left cheek garment portions 122, 124 and across the posterior head garment portion 128 (e.g., each of such pressure applying regions may be separate chambers supplied by separate fluid conduits). As described herein, when a garment portion is described as including one or more pressure applying regions, such one or more pressure applying regions may be a separate pressure applying region or may be a pressure applying regions shared with one or more other garment portions (e.g., torso garment portions and posterior head garment portions may use the same pressure applying region to apply compression to a body portion associated therewith).

However, such head pressure applying regions 121 may include any number of different and separate chambers along the wrappable length of the head garment portion 120 and controllable to produce such desired lymph movement. For example, the head pressure applying regions 121 may be separable between the right and left cheek garment portions 122, 124 (e.g., alone dotted line 191) and the posterior head garment portion 128. In other words, the head pressure applying regions 121 may be separated in any suitable way that may allow pressure to be applied from the right and left cheeks (e.g., proximate the anterior of the head) towards the posterior of the head and/or from the top of the posterior of the head towards the neck (e.g., to move lymph from the cheeks towards the neck at the posterior of the head). For example, the head pressure applying regions 121 may be separated such that each head pressure applying region 121 may be independently controllable to move lymph in a desired direction (e.g., as shown in FIGS. 2-4).

Although not shown, in one or more embedment's, the head garment portion 120 may further include a forehead garment portion configurable to apply pressure to a portion of the forehead. The forehead garment portion may include one or more forehead pressure applying regions controllable to apply pressure to a portion of the forehead.

A plan view of the exemplary torso garment portion 140 including one or more torso pressure applying regions 141 labeled B1, B2, B3, B4, B5, B6, B7, & B8 are shown in FIG. 5A. Although as shown the torso garment portion 140 may include eight torso pressure applying regions 141, any number of torso pressure applying regions 141 may be implemented or utilized. In one or more embodiments, it may be described that at least a portion of the one or more torso pressure applying regions 141 may define an arcuate shape (e.g., curved portions of the torso pressure applying regions 141 extending over the shoulders of a user from the posterior to the anterior). For example, arcuate shapes (e.g., of any of the portions of the garment) that may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference. The one or more torso pressure applying regions 141 may be configured to be controlled (e.g., using controller 102 as shown in FIG. 1) to apply pressure to one or more portions of the torso when the torso garment portion 140 is positioned on the torso.

The one or more torso pressure applying regions 141 may be located in various locations within the torso garment portion 140 to apply pressure to a variety of different locations on the torso. For example, the torso garment portion 140 may include a right torso garment portion 151 positionable proximate the right side of the torso, a left torso garment portion 152 positionable proximate the left side of the torso, and a posterior torso garment portion 150 positionable proximate the posterior of the torso. The one or more torso pressure applying regions 141 associated with the right, left, and posterior torso garment portions 151, 152, 150 may be controllable to apply pressure to the right side, left side, and posterior of the torso, respectively. In one or more embodiments, the right torso garment portion 151 may be described as positioned proximate a right anterior portion and right side of the torso and the left torso garment 152 may be described as positionable proximate a left anterior portion and a left side of the torso;

the torso pressure applying regions 141 associated with such regions may be controllable or configured to apply pressure to each of the right and left anterior portions of the torso and the right and left sides of the torso.

In one or more embodiments, each of the one or more torso pressure applying regions 141 may be configured in any suitable manner such that the regions 141 may be controlled to apply pressure to a portion of the torso to move lymph as desired. For example, the one or more torso pressure applying regions 141 may include fluid chambers or cells, pneumatic pressure applying regions, actuatable elements applying pressure to regions, hydraulic pressure applying regions, etc. Specifically, the one or more torso pressure applying regions 141 may include one or more chambers configured to receive fluid (e.g., air).

For example, in one or more embodiments, the one or more torso pressure applying regions 141 may be configured to apply pressure to a portion of the torso using the one or more chambers through the control of fluid provided thereto, e.g., liquid flow, air flow, etc. For example, the torso garment portion 140 may include one or more torso garment ports 159 (a few of which are labeled in FIG. 5A) through which fluid may be provided to the one or more chambers (e.g., such as with use of pump 103 shown in FIG. 1, under control of controller 102 with use of a sensor feedback system).

Further, in one or more embodiments, the one or more torso pressure applying regions 141 may include one or more torso actuatable elements configured to apply pressure to a portion of the torso (e.g., an electrical signal may be used to actuate an element within the garment, such as electrically actuatable fibers in the garment, such that the compartment including such fibers applies a pressure to a portion of the body). In one or more embodiments, the one or more torso pressure applying regions 141 may include both one or more chambers configured to receive fluid and one or more torso actuatable elements.

Further, in one or more embodiments, the right torso garment portion 151 may include a right chest garment portion 142 positionable proximate the right shoulder and chest of the torso and a right lower anterior torso garment portion 144 positionable proximate the right under arm and right waist of the torso. The right chest garment portion 142 may include one or more right chest pressure applying regions controllable to apply pressure to a portion of the right chest and right shoulder. The right lower anterior torso garment portion 144 may include one or more pressure applying regions controllable to apply pressure to a portion of the lower anterior side of the torso.

Still further, the left torso garment portion 152 may also include a left chest garment portion 143 positionable proximate the left shoulder and chest of the torso and a left lower anterior torso garment portion 148 positionable proximate the left under arm and left waist of the torso. The left chest garment portion 143 may include one or more left chest pressure applying regions controllable to apply pressure to a portion of the left chest and left shoulder. The left lower anterior torso garment portion 148 may include one or more left axillary pressure applying regions controllable to apply pressure to a portion of the lower anterior side of the torso. Each of the pressure applying regions 141 of the torso garment portion 140 may be controllable to apply pressure to a portion of the torso to move lymph as desired (e.g., downward from the neck and shoulder regions to lower portions of the torso).

Any number of pressure applying regions 141 may be configured in the torso garment portion 140 such that they may be controlled to move lymph as described, for example, with reference to FIGS. 2-4. For example, as shown in FIG. 5A, a plurality of pressure applying regions 141 are distributed in the torso garment portion 140. In one or more embodiments, the plurality of pressure applying regions 141 may include an upper torso pressure applying region 261 positionable for applying pressure to the upper posterior torso region and upper anterior torso region of the body 10. Further, in one or more embodiments, the plurality of pressure applying regions 141 may include a lower posterior torso pressure applying region 263 positionable for applying pressure primarily to the lower posterior torso region of the body 10.

One or more of the pressure applying regions 141 may extend along one of the left or right chest garment portions 143, 142. For example, one or more of the pressure applying regions 141 may extend within the left chest garment portion 143 from the left lower anterior torso garment portion 148 to an upper torso pressure applying region 261 to the lower posterior torso pressure applying region 263 and to the left wraparound portion 107. Further, for example, one or more of the pressure applying regions 141 may extend within the right chest garment portion 142 from the right lower anterior torso garment portion 144 to an upper torso pressure applying region 261 to the lower posterior torso pressure applying region 263 and to the right wraparound portion 108.

Figure 10:
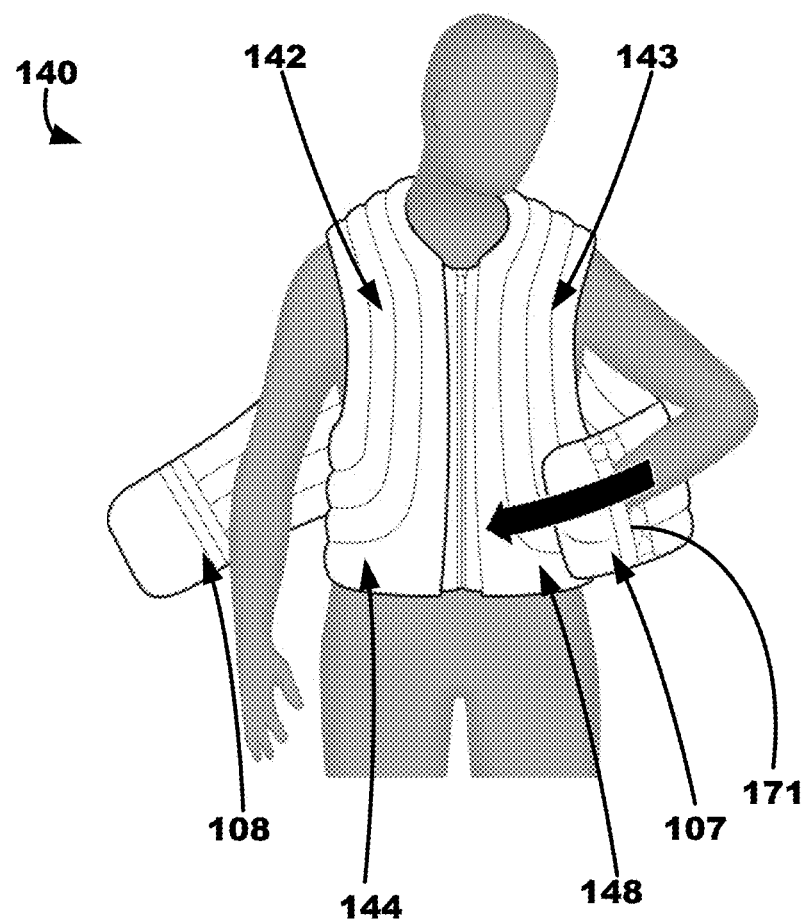
FIGS. 10-11 are front views of the torso garment portion of FIG. 5A being further coupled, or secured, around the body.
Figure 11:
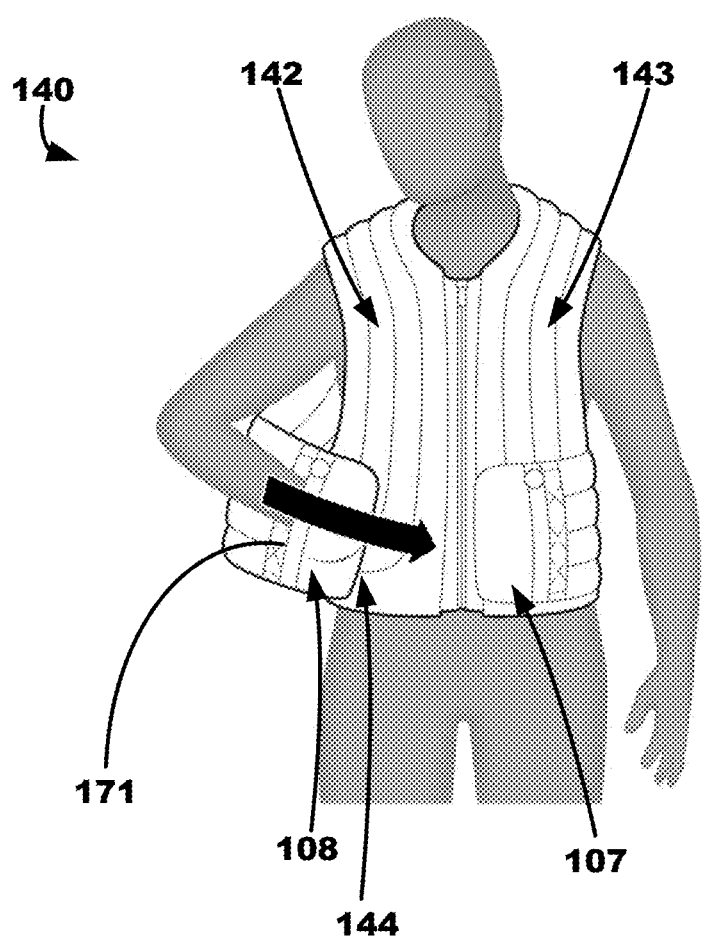
Figure 12:
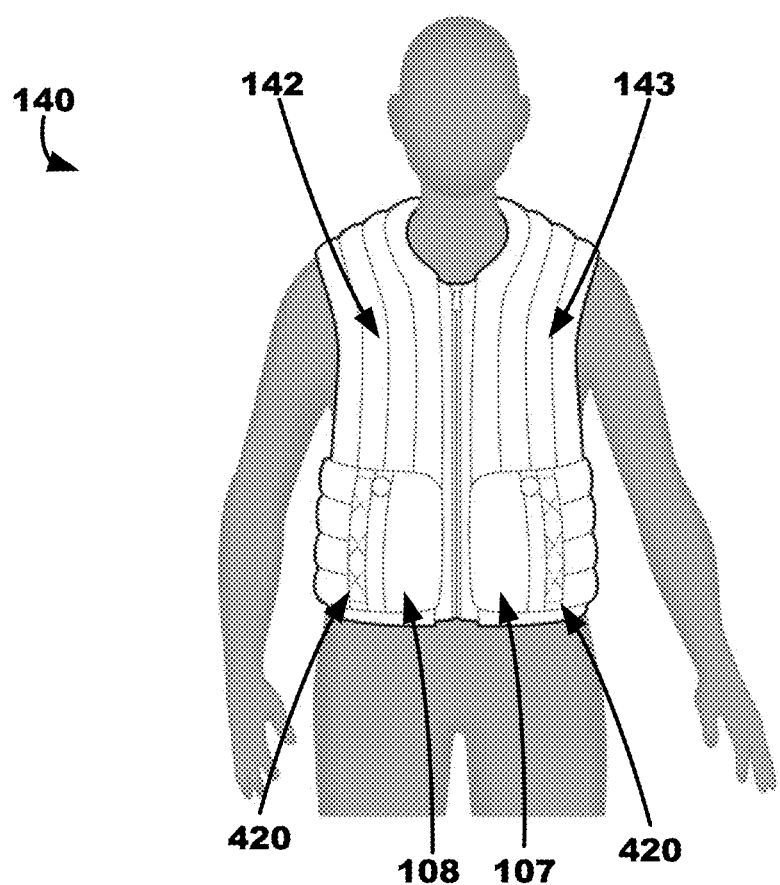
FIG. 12 is a front view of the torso garment portion of FIG. 5A after being donned and coupled to the body.

In one or more embodiments (e.g., as shown in FIGS. 1 and 10-12), the right wraparound portion 108 may be configured to overlap the right lower anterior torso garment portion 144 and the left wraparound portion 107 may be configured to overlap the left lower anterior torso garment portion 148 to, e.g., further tighten or secure the torso garment portion 140 about the body 10 after, e.g., the right chest garment portion 142 is coupled to the left chest garment portion 143 as will be further described herein with respect to FIGS. 10-12. Further, in one or more embodiments and/or depending on the size of the body with respect to the size of the torso garment, the right wraparound portion 108 may be configured to overlap the midline of the torso and over to the left lower anterior torso garment portion 148, and likewise, the left wraparound portion 107 may be configured to overlap the midline of the torso to the right lower anterior torso garment portion 144.

As shown in FIG. 1, each of the head garment portion 120, the neck garment portion 110, and the torso garment portion 140 may be configured in a symmetrical manner generally with reference to the axis of a person's body. In other words, the various garment portions include sub-portions symmetrical about an axis. For example, the head garment portion 120 as shown in FIG. 1 is symmetrical about axis 201 (e.g., one or more sub-portions, such as right cheek garment portion 122 and left cheek garment portion 124 may be symmetrical about axis 201). In one or more embodiments, sub-portions of one or more of the head garment portion 120, the neck garment portion 110, and the torso garment portion 140 which include pressure applying regions may be symmetrical about axis 201, while other portions the head garment portion 120, the neck garment portion 110, or the torso garment portion 140 may be non-symmetrical. Further, in one or more embodiments, non-symmetrical garments are contemplated within the present disclosure (e.g., various garment portions may be non-symmetrical to accomplish one or more various functions such as related to donning or securing the garment on a user).

In one or more embodiments, the one or more pressure applying regions of the head garment portion 120, the neck garment portion 110, and the torso garment portion 140 may be used in conjunction with one another. For example, the one or more neck pressure applying regions 111 may be controllable to apply a pressure to the portion of the neck after the one or more head pressure applying regions 121 are controlled to apply pressure to a portion of the head. In another example, the one or more neck pressure applying regions 111 may be controllable to apply pressure to the portion of the neck and the one or more head pressure applying regions 121 may be controllable to apply pressure to the portion of the head to move lymph from the head towards the neck and downward therefrom. In yet another example, the one or more under chin pressure applying regions 126, the one or more cheek pressure applying regions 123, the one or more posterior head pressure applying regions 129, and the one or more neck pressure applying regions 111 may be configured or controllable to move lymph from a portion under the chin towards the portion of the cheek, from the portion of the cheek towards the portion of the posterior head, and from the portion of the posterior head towards the portion of the neck.

In one or more embodiments, the controller (e.g., controller 102 as shown in FIG. 1) may be configured to control pressure applied by each of the one or more head pressure applying regions 121, the one or more neck pressure applying regions 111, and the one or more torso pressure applying regions 141 to move lymph at least from the head to the neck to the torso. In one or more embodiments, each of the head and torso pressure applying regions 121, 141 may be controllable to apply pressure to move lymph at least from the left and right sides of the head towards the posterior of the head and from the posterior of the head downward towards the torso.

In one or more embodiments, the torso garment portion 140 may be coupled to the neck garment portion 110 about labels "A" and "B" as shown in FIGS. 5A-5B. Any suitable manner may be used to couple the torso and neck garment portions 140, 110. For example, such garment portions may be coupled using stitching, welding, or any other coupling technique to form a unitary garment. In one or more embodiments, the torso garment portion 140 may be removably couplable to the neck garment portion 110, for example, using flaps extending outward from one or both of the torso garment portion 140 and the neck garment portion 110. In other words, the torso garment portion 140 and the neck garment portion 110 may be coupled and uncoupled using any suitable fastener at, e.g., the flaps extending outward from one or both.

In one or more embodiments, the head garment portion 120 and the torso garment portion 140 may be coupled to the neck garment portion 110. For example, the head garment portion 120 may be coupled to the neck garment portion 110, and, any suitable manner may be used to couple the torso or neck garment portions 140, 110 and the head garment portion 120. For example, such garment portions may be coupled using stitching, welding, or any other coupling technique to form a unitary garment.

Further, in one or more embodiments, the head, neck, and torso garment portions 120, 110, 140 may be coupled to one another in a variety of different ways. For example, the torso garment portion 140 may be coupled to the neck garment portion 110 such that the torso garment portion 140 has increased flexibility to move relative to the neck garment portion 110. For example, the neck and torso garment portions 140, 110 may be coupled to one another such that there are one or more openings between the neck and torso garment portions 140, 110 proximate the posterior of the neck. In one or more embodiments, the torso garment portion 140 may be coupled to the head garment portion 120 (e.g., directly coupled). For example, in one or more embodiments, the head garment portion 120 and the neck garment portion 110 may be provided as a single head/neck garment portion that may be coupled to the torso garment portion 140). In other words, coupling of the head and neck garment portions may include such garment portions being formed as a single unitary garment portion. In one or more embodiments, the torso garment portion 140 may be removably couplable to the neck garment portion 110 and/or the head garment portion 120, for example, using flaps extending outward from one or each of the torso garment portion 140, the head garment portion 120, and the neck garment portion 110. For example, the torso garment portion 140 may have flaps extending from the torso garment portion 140 proximate the neck such that the flaps may have the appearance of a "popped-up" collar. Therefore, the torso garment portion 140 may be coupled and uncoupled to the head garment portion 120 and/or the neck garment portion 110 using any suitable fastener at, e.g., the flaps extending outward from one or both.

A cross-section of a portion 800 of an exemplary garment including one or more cells 801 which may be used in providing any of the garments described herein is shown in FIG. 23A. The garment portion 800 may define an exterior surface 802 configured to face the exterior, e.g., away from a user when wearing the garment portion 800, and an opposing interior surface 803 configured to face the interior, e.g., towards a user wearing the garment portion 800. The interior surface 803 may be configured to be positioned closer to the human body than the exterior surface 802 when the garment portion 800 is positioned on the body. As shown, the garment portion 800 defines a plurality of chambers configured and corresponding to pressure applying regions. Each of the chambers 801 defines a volume 805 that may be separated in any way that isolates the volume 805 of a chamber from the volumes of the other chambers 801 (e.g., such that the chambers. For example, the volumes 805 of the chambers 801 may be separated by welds 815, e.g., welds between one or more layers of the garment portion 800 as will be further described herein. The volumes, or cavities, 805 defined by, or in each, of the chambers 801 may be configured to receive a fluid. The fluid may be received from a source (e.g., from pump 103 shown in FIG. 1) to apply pressure at a pressure applying region of the garment to a body portion when garment portion 800 is worn by a user. For example, fluid may be directed to each of the volumes 805 of the chambers 801 in a sequential or non-sequential manner.

Further, each of the various pressure applying regions described herein may include, e.g., one of the one or more chambers 801 or a plurality of the chambers 801. In one or more embodiments, different pressure applying regions described herein may include, e.g., the same one or more chambers, but may, e.g., be positioned at different locations on the garment.

The garment portion 800 may include one or more layers from the exterior surface 802 to the interior surface 803. For example, the exterior facing layer 806, or the layer defining the exterior surface 802, may include one or more fabric materials so as to define a "hook" surface on the exterior surface 802 for coupling to a "loop" surface or material forming, or defining, a "hook-and-loop" fastener. The exterior surface of the exemplary garment portions described herein may be partially or completely defined by a "hook" surface for use in a "hook-and-loop" fastener.

A foam layer 807 may be adjacent the exterior facing layer 807, and then a polymer layer 808 (e.g., polyurethane, polyvinyl, etc.) may be located adjacent the foam layer 807 facing the volume 803 of the chamber 801. The interior side of the garment portion 800 may be similar to the exterior side except that, instead of a exterior facing layer, the foam layer 807 may be adjacent a fabric layer 809 configured to be located adjacent the torso of a body.

Figure 23B:
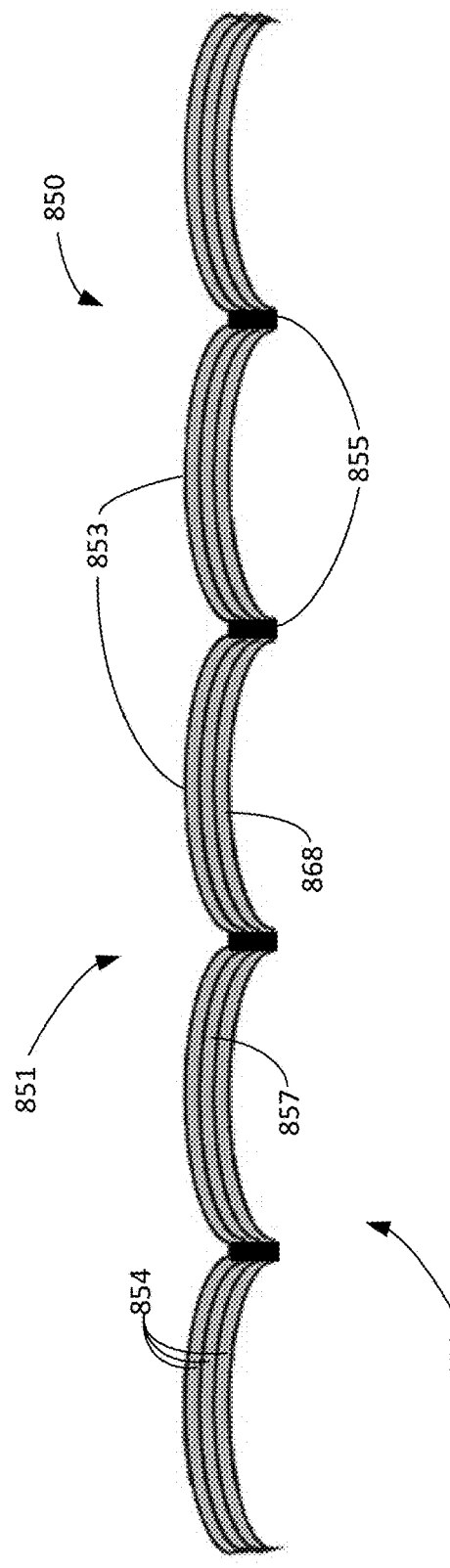
FIG. 23B is a cross-sectional view of one or more cells including actuatable elements (e.g., without inflatable chambers or cells) of an exemplary compression garment that may be used with one of the exemplary garment portions such as shown in FIGS. 1 and 5-19.

A cross-section of another portion 850 of exemplary garment including one or more compression regions 853 which may be used in providing any of the garments described herein is shown in FIG. 23B. The garment portion 850 may define an exterior surface 851 and an opposing interior surface 852. The interior surface 852 may be configured to be positioned closer to the human body than the exterior surface 851 when the garment portion 850 is positioned on the body. The one or more regions 853 may be separated or may not need to be separated from one another. In one embodiment, for example, the one or more regions 853 may be separated by welds 855.

The garment 850 may include one or more layers 854, with at least one of the one or more layers 854 including a compression layer 857. The compression layer 857 may include a variety of suitable components configured to apply pressure. For example, the pressure may be applied through the compression layer by an air or pneumatic system, a hydraulic system, an electro-mechanical system, actuated elements (e.g., an electrical signal may be used to actuate an element within the garment, such as electrically actuatable fibers in the garment, such that the compartment including such fibers applies a pressure to a portion of the body), a cable/lace tensioning system, or any other system that is configured to apply pressure to the portion of the body through the garment portion 850.

In at least one embodiment, the compression layer 857 may be a plurality of actuated elements configured to apply pressure to the portion of the body (e.g., actuatable material, such as nitinol, or any other compressing devices). The compression layer 857 of each of the one or more regions 853 may apply pressure to body portion when the garment portion 850 is worn by a user. For example, pressure may be applied by each of the one or more regions 853 in a sequential or in a continuous manner over the one or more regions 853. Each of the various pressure applying regions described herein may include, e.g., one of the one or more regions 853 or a plurality of the one or more regions 853. In one or more embodiments, different pressure applying regions described herein may include, e.g., the same one or more regions, but may, e.g., be positioned at different locations on the garment portion 850.

The garment portions 850, described in FIG. 23B (which may be used in any of the compression garments and portions thereof described herein), may also be associated with one or more pressure sensors 868 configured to measure pressure applied to the portion of the body by the garment portions 850. The pressure sensors 868 may be located at a variety of positions along the garment portion 850. For example, the pressure sensors 868 may be positioned (e.g., at an equal distance apart or as necessary) along the length of the garment portion 850. The pressure sensors 868 may be located adjacent the one or more of the pressure applying regions or multiple layers 854 of the garment portion 850.

For example, one layer of material may encompass pressure sensors 868 including pressure sensing regions corresponding to the one or more pressure applying regions and/or corresponding to the one or more chambers 801, 853. In one or more embodiments, the pressure sensors 868 may be positioned on a side of the garment portions 800, 850 that may be proximate the portion of the body (e.g., the interior surface 802, 852, etc.). The pressure sensors 868 may be positioned for sensing pressure at, e.g., each pressure applying region, each of the one or more chambers 801, 853, a manifold for multiple chambers, etc.

Pressure sensor apparatus may be implemented for sensing pressure in a plurality of different manners at, e.g., each pressure applying region, each air cell or chamber, a manifold for multiple chambers, etc. The pressure sensor apparatus may be configured to measure pressure in a variety of different ways, e.g., one sensor for each pressure applying region, a single sensor for all of the pressure applying regions, etc. Additionally, the controller may be configured to control the pressure applied to the portion of the body based on the measured pressure. For example, pressure sensing apparatus may take the form of using pressure sensors within the garment as described in U.S. Pat. No. 9,027,408 entitled "Elastomeric Particle Having An Electrically Conducting Surface, A Pressure Sensor Comprising Said Particles, A Method For Producing Said Sensor And A Sensor System Comprising Said Sensors," or a pump or control apparatus (e.g., 102) may be provided with pressure sensing functionality (e.g., measuring pressures of air in chambers as part of the pump apparatus) such as described in U.S. Pat. No. 7,947,003 entitled "Pressurized Medical Device," all of which are incorporated by reference herein.

Donning the torso garment portion 140 is depicted in FIGS. 7-13. The torso garment portion 140 may further include right and left posterior adjustment portions 190, 192 configure to adjust torso garment portion 140 to properly fit around the circumference, or bust, of the torso of the body 10 prior to donning the torso garment portion 140. The right posterior adjustment portion 190 may extend from the right lower anterior torso garment portion 144 and the left posterior adjustment portion 192 may extend from the left lower anterior torso garment portion 148 as shown in FIG. 5A. The right posterior adjustment portion 190 may be configured to wrapped around the right posterior of the torso of the body 10 as indicated by the "wraparound" arrow and be removably coupled to the left posterior adjustment portion 192, which is configured to wrapped around the left posterior of the torso of the body as also indicated by the other "wraparound" arrow. The coupling of the right posterior adjustment portion 190 to the left posterior adjustment portion 192 may be defined the size around the torso about which the torso garment portion 140 may fit (e.g., to define the snugness or tightness of the torso garment portion 140 around the torso of the body 10). To facilitate or provide the coupling between the right posterior adjustment portion 190 and the left posterior adjustment portion 192, each of the right and left posterior adjustment portions 190, 192 may include hook-and-loop fasteners configured to be coupled to each other. Further, when the torso garment portion 140 is being adjusted, the right posterior adjustment portion 190 may be coupled to the left posterior adjustment portion 192 to vary the size of the torso garment portion 140 as illustrated by the large, horizontally opposed arrows in FIG. 7. For example, the right posterior adjustment portion 190 may be pulled closer to the left posterior adjustment portion 192 when coupling for a smaller, tighter fit while the right posterior adjustment portion 190 may be located further away from the left posterior adjustment portion 192 when coupling for a larger, looser fit.

Figure 7:
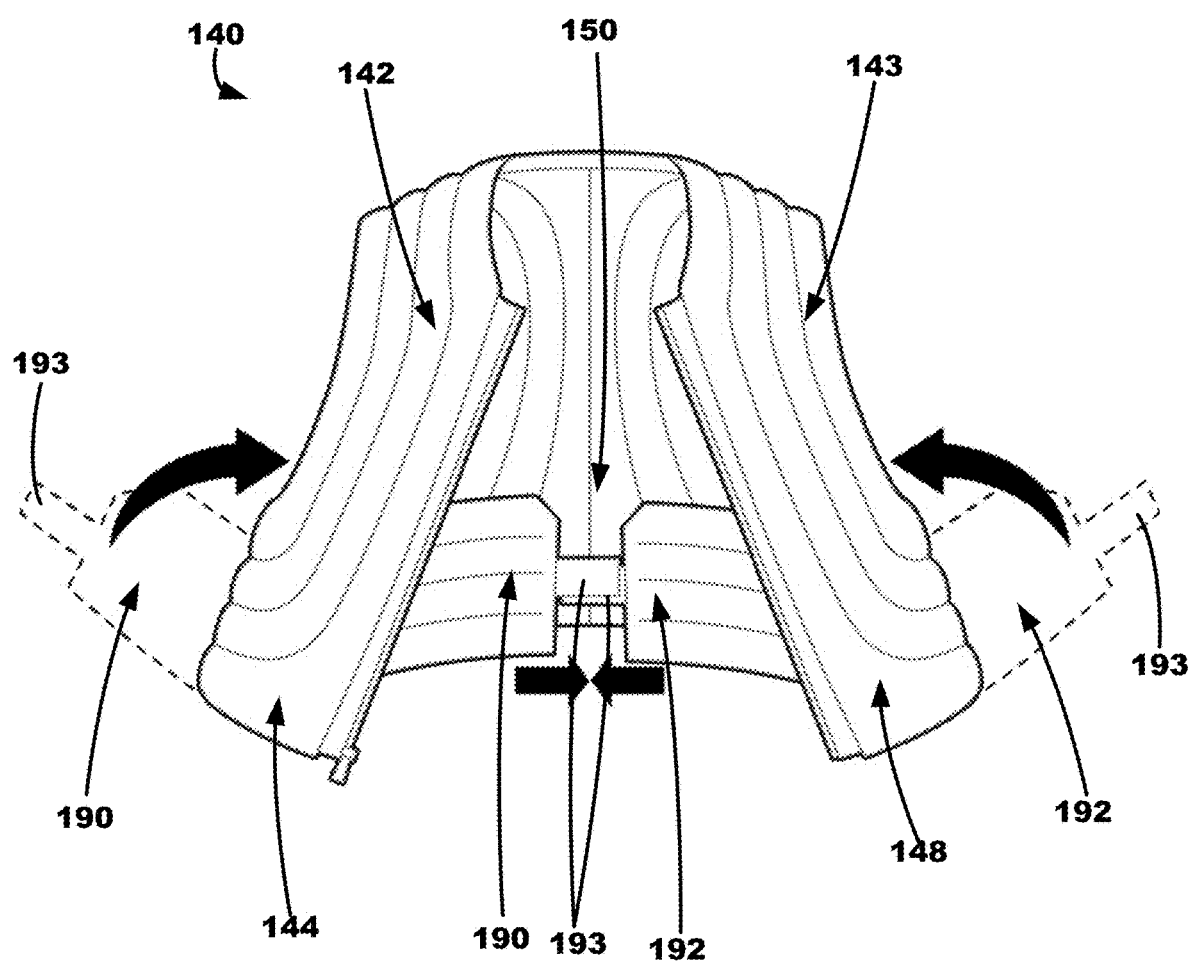
FIG. 7 is a front view of the torso garment portion of FIG. 5A being configured to be donned by a body.

Additionally, as shown in FIG. 7, the right posterior adjustment portion 190 and the left posterior adjustment portion 192 may be configured to be located on the "inside" of the posterior torso garment portion 150 when being donned. In one or more embodiments, the posterior torso garment portion 150 may be removably coupled to the right posterior adjustment portion 190 and the left posterior adjustment portion 192 through, e.g., hook-and-loop fasteners, so as to secure the posterior torso garment portion 150 to be located proximate the posterior of the torso of the body 10. Generally, the right posterior adjustment portion 190 and the left posterior adjustment portion 192 may be adjusted and coupled prior to coupling the posterior torso garment portion 150 thereto because, e.g., coupling of the posterior torso garment portion 150 to the right posterior adjustment portion 190 and the left posterior adjustment portion 192 may limit, or restrict, the adjustment of the right posterior adjustment portion 190 with respect to the left posterior adjustment portion 192. In other words, the coupling of the posterior torso garment portion 150 to the right posterior adjustment portion 190 and the left posterior adjustment portion 192 may further secure, or couple, the right posterior adjustment portion 190 to the left posterior adjustment portion 192 to, e.g., maintain the connection therebetween.

Figure 8:
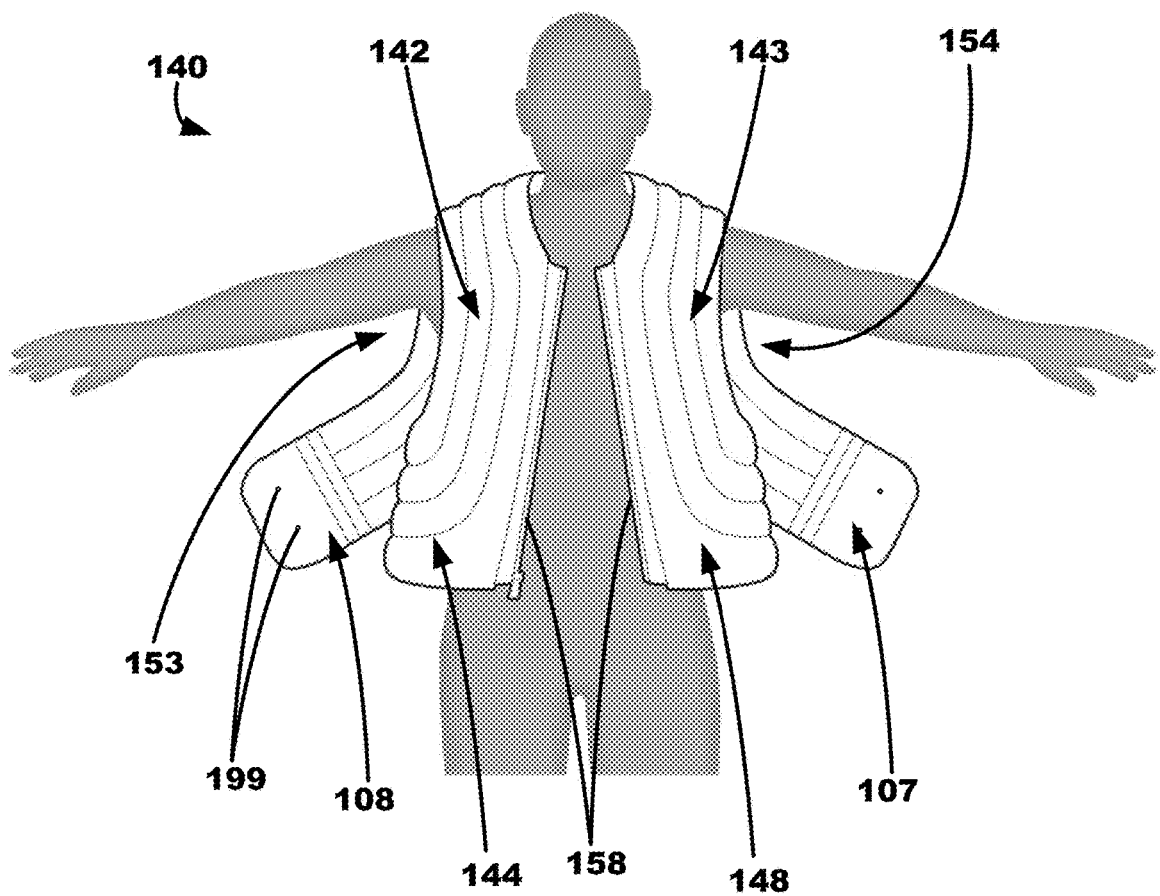
FIG. 8 is a front view of the torso garment portion of FIG. 5A being donned on the body.
Figure 9:
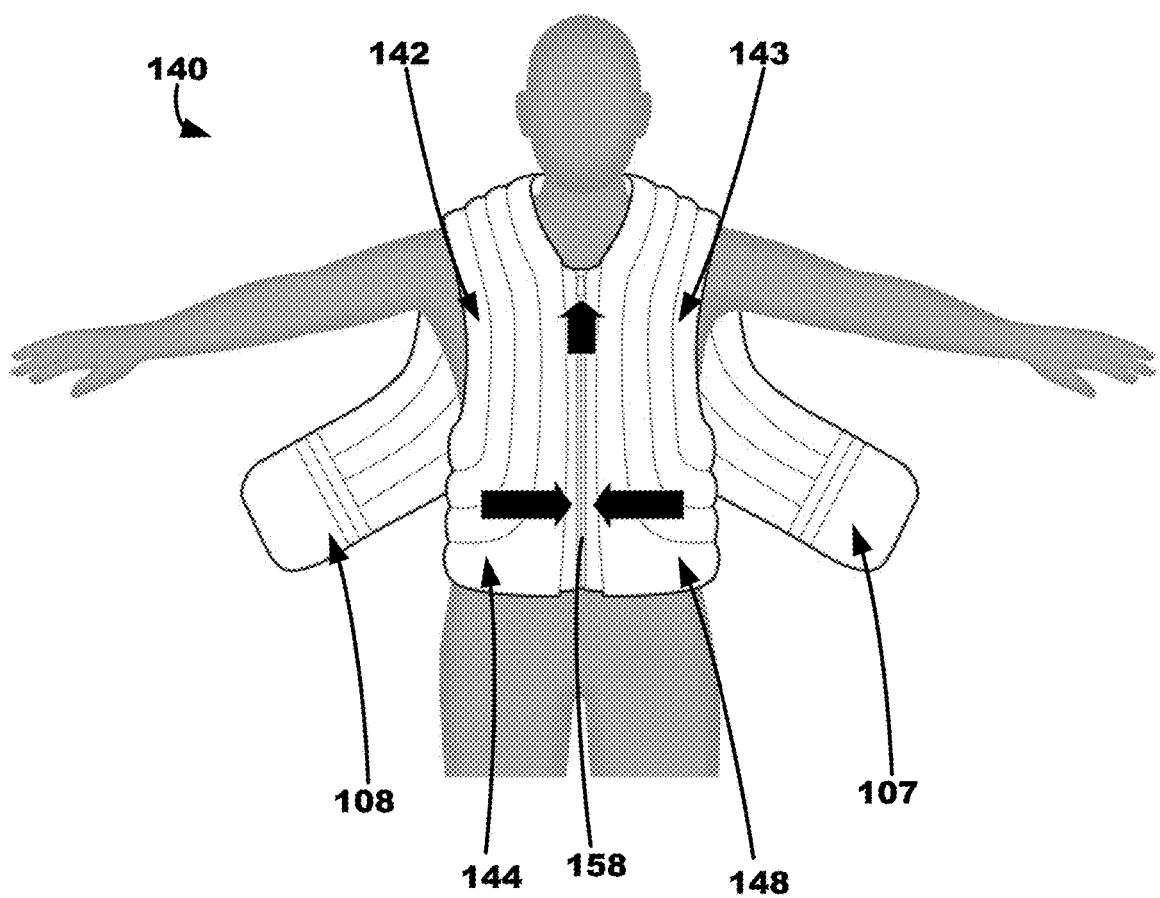
FIG. 9 is a front view of the torso garment portion of FIG. 5A being coupled around the body.

The torso garment portion 140 may then be located on the torso of the body 10 as shown in FIG. 8. More specifically, the neck of the body 10 may be positioned through the neck aperture and the arms of the body 10 may be positioned through the right and left arm openings 153, 154 such that the posterior, or back, of the torso is proximate, or adjacent, the posterior torso garment portion 150 and the right and left posterior adjustment portions 190, 192. The right chest garment portion 142 may now be coupled to the left chest garment portion 143 using, e.g., the zipper 158, as shown in FIG. 9.

Next, to further secure, or tighten, the torso garment portion 140 about the torso of the body 10, a user may place a hand in a mitt opening such as the left mitt opening 171 of the left wraparound portion 107 shown in FIG. 10 and then move the left wraparound portion 107 around the left anterior of the torso over the left lower anterior garment portion 148 for coupling thereto with, e.g., hook-and-loop fasteners. The movement and coupling of the left wraparound portion 107 may tighten the torso garment portion 140 about the torso to, e.g., provide a snug fit. Likewise, a user may place a hand in a mitt opening such as the right mitt opening 172 of the right wraparound portion 108 shown in FIG. 11, and then move the right wraparound portion 108 around the right anterior of the torso over the right lower anterior garment portion 144 for coupling thereto with, e.g., hook-and-loop fasteners. The movement and coupling of the right wraparound portion 108 may further tighten the torso garment portion 140 about the torso to, e.g., provide a snug fit. In one or more embodiments, each of the mitt openings 171, 172 may be sized, or define a size, such that a majority of not all of a human hand may fit within the mitt openings 171, 172 so as, e.g., provide a large opening to receive a human hand when the wraparound portions 107, 108 are located in awkward position for the human user to grasp (e.g., behind or partially-behind the user's back, hanging below the user's waistline, etc.). Further, it may be described that the mitt openings 171, 172 are part of a mitt apparatus, or mitt, located proximate the end region of the respective wraparound portion 107, 108. Still further, it may be described that the mitt apparatus, or mitt, may terminate the end region of the wraparound portion 107, 108. In other words, the distal end regions of the wraparound portions 107, 108 may include mitts, or mitt apparatus, which define the mitt openings 171, 172. Additionally, as depicted on FIG. 8, the hook-and-loop fastener surface of the wraparound portions 107, 108 may include "spot welds" or "button welds" 199 to, e.g., resist the hook-and-loop fastener surface from "tenting" when attaching and un-attaching the wraparound portions 107, 108 from the remainder of the torso garment portion 140.

After the right wraparound portion 108 is coupled to the right lower anterior garment portion 144 as shown in FIG. 12, the torso garment portion 140 may be further tightened using tightening apparatus 420 (e.g., lacing systems). For example, as shown, tightening apparatus 420 may be part of each of the wraparound portions 107, 108 such that tightening apparatus 420 may extend or shorten the length of the wraparound portions 107, 108. Further, it may be generally described that the tightening apparatus 420 may configured to further assist in positioning (e.g., tightening) the torso garment portion 140 on the torso of the body.

Figure 17A:
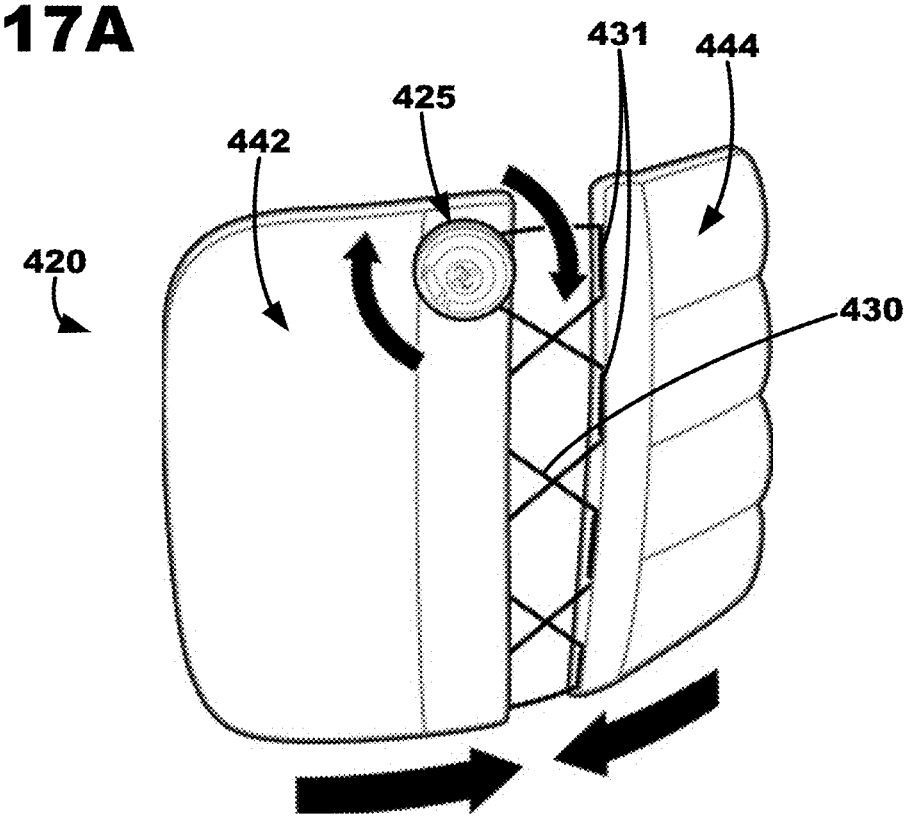
FIGS. 17A-17B are perspective views of an exemplary tightening apparatus (e.g., a lacing system) for use within the exemplary compression system of FIG. 12 to assist in donning one or more garment portions thereof.
Figure 17B:
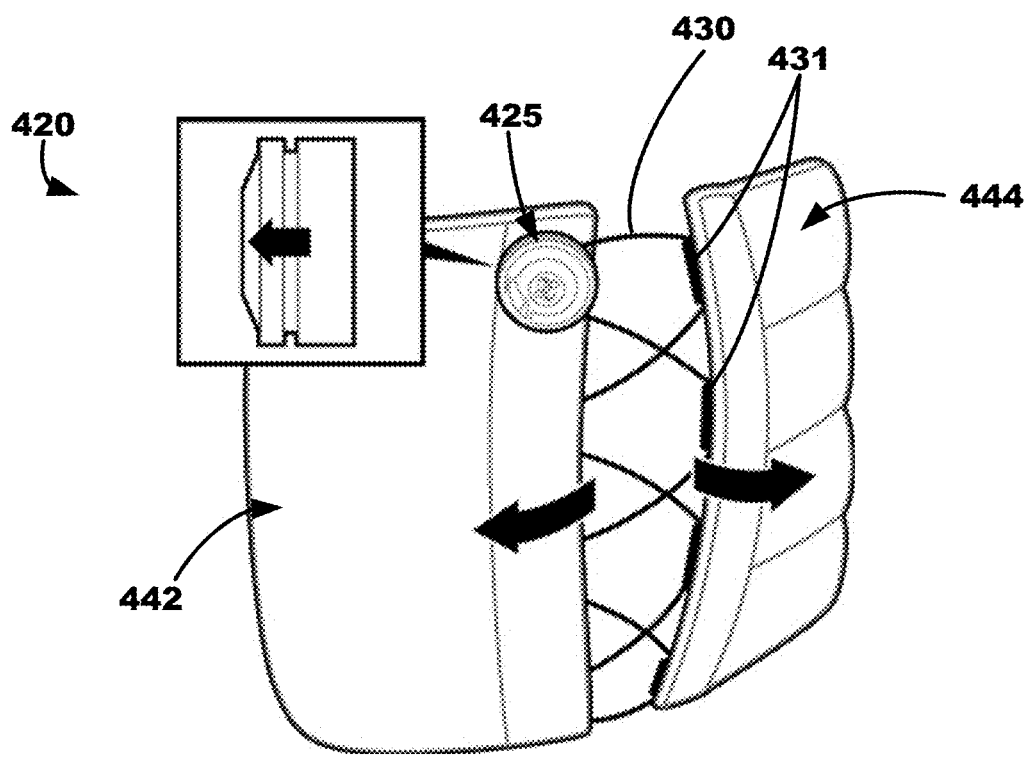

Generally, as shown in FIGS. 17A-17B, the tightening apparatus 420 may be configured, or operable, to move a first portion 442 of a wraparound portion relative to a second portion 444 of the wraparound portion to, e.g., assist in tightening the torso garment portion 140 proximate the torso of the body. The tightening apparatus 420 may include one or more laces 430 positioned (e.g., laced) between the first and second portions 442, 444. In one or more embodiments, the one or more laces 430 may be guided between the first and second portions 442, 444 using guide members 431 (a few of which are labeled in FIGS. 17A-17B). The tightening apparatus 420 may also include a tightening device 425 that may be coupled to the one or more laces 430 and configured to apply tension on the one or more laces 430 to either shorten or lengthen the distance between the first portion 442 and the second portion 444 of the wraparound portions, e.g., to tighten the torso garment portion 140 about the torso of the body 10. More specifically, the tightening device 425 may be rotated one direction to lengthen the distance between the first portion 442 and the second portion 444 and rotated the opposite direction to shorten the distance between the first portion 442 and the second portion 444. Additionally, the tightening device 425 may define, or be configured into, a locked position, in which the tightening device 425 cannot be rotated (e.g., as shown be the zoomed in view of the tightening device 425). In one or more embodiments, the tightening device 425 may be centering vertically on the tightening apparatus 420 to, e.g., to improve lacing efficiency, ease of use, etc.

As shown in FIG. 12, the tightening apparatus 420 are located proximate the left and right lower anterior garment portions 144, 148 and as part of the left and right wraparound portions 107, 108, e.g., for convenient access by the hands of a user. Also, the tightening apparatus 420 may be located in any other location along the garment that may need additional help in tightening or adjusting the garment proximate the body. The tightening apparatus 420 described herein may be similar to and include one or more features found in PCT International Application No. PCT/US2015/036951 entitled "Compression Garment System with Tightening Apparatus," which is herein incorporated by reference.

Figure 13:
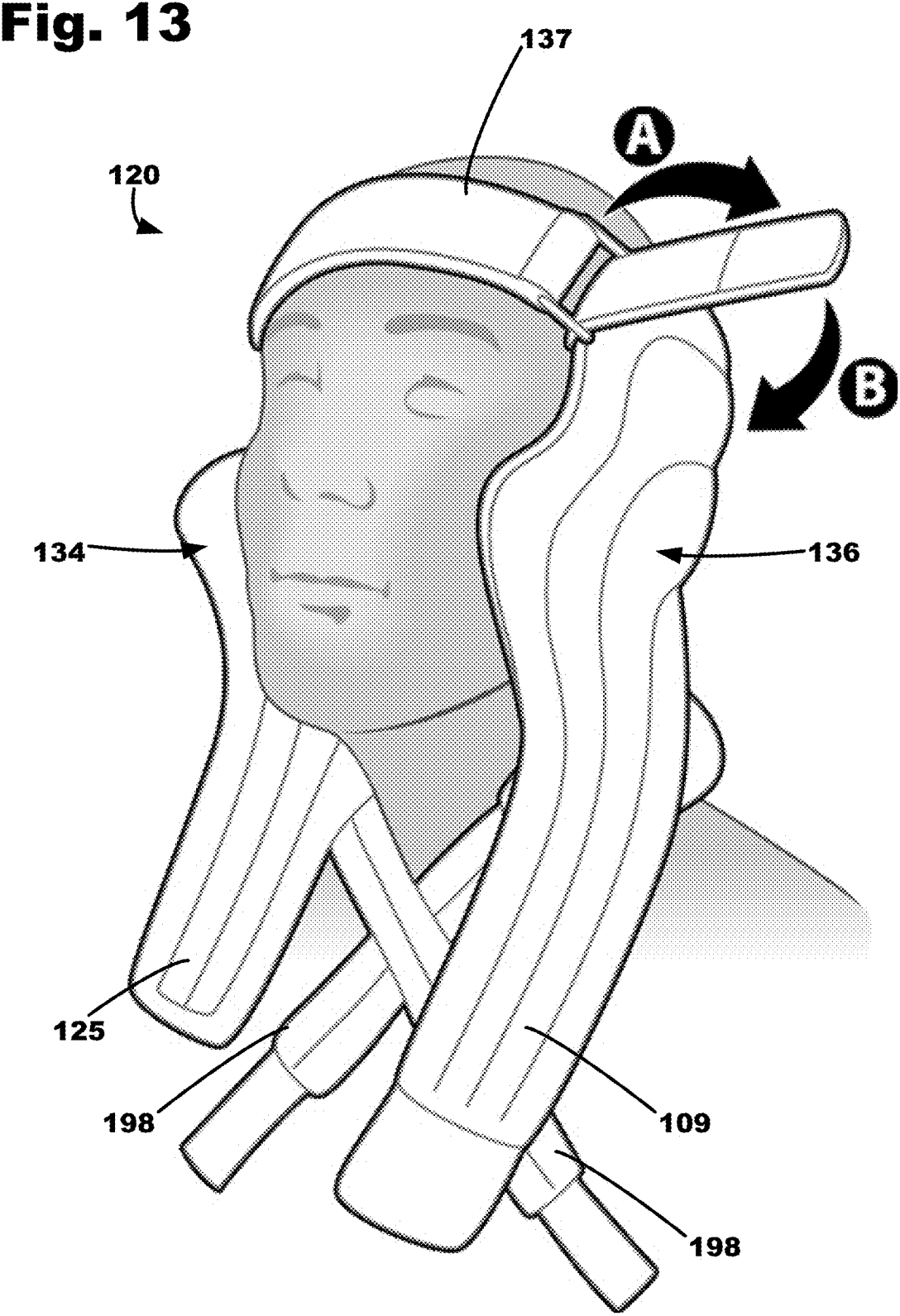
FIG. 13 is a front perspective view of the head garment portion of FIG. 5A being donned on a head.
Figure 14:
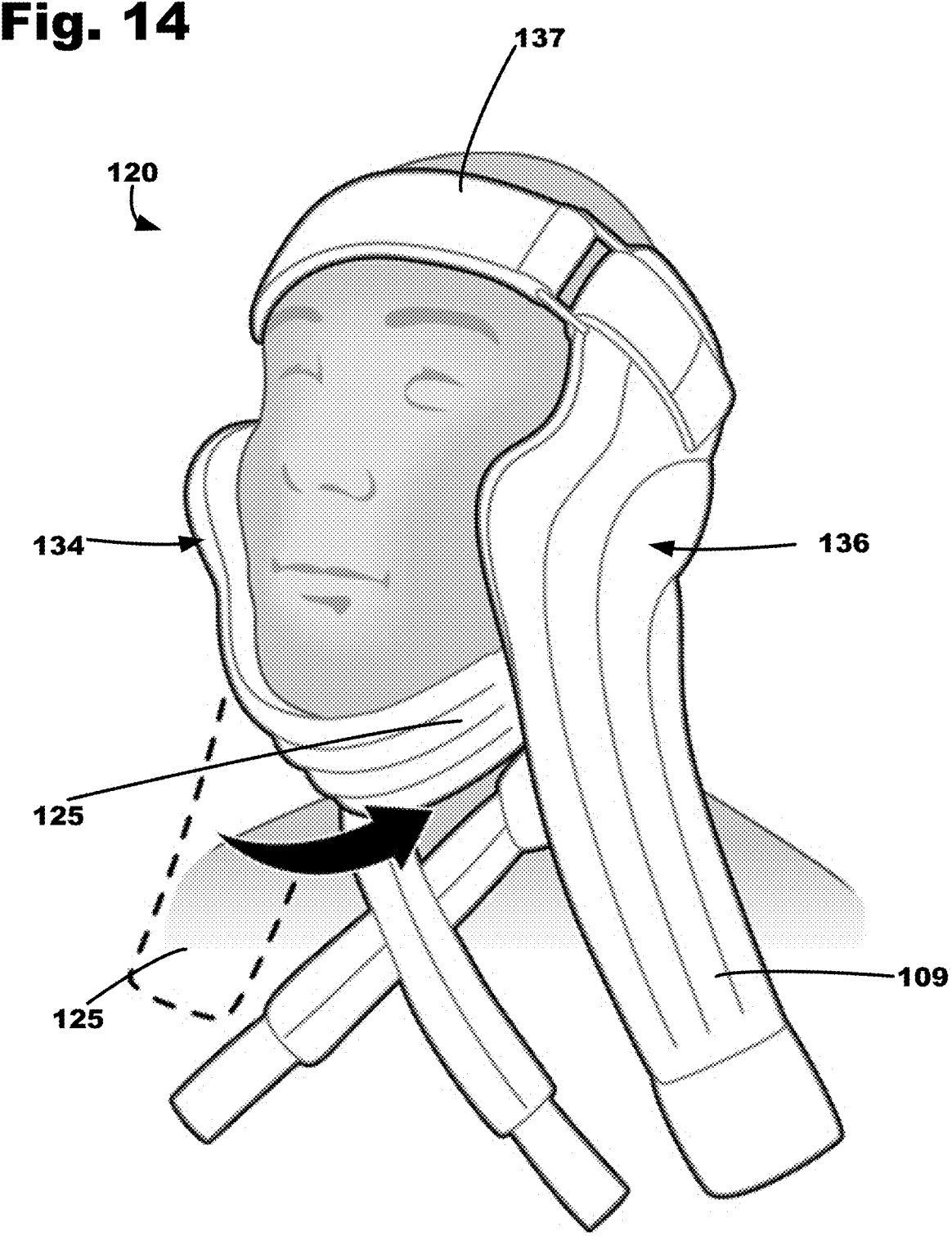
FIG. 14 is a front perspective view of the head garment portion of FIG. 5A being coupled about the chin of the head.
Figure 15:
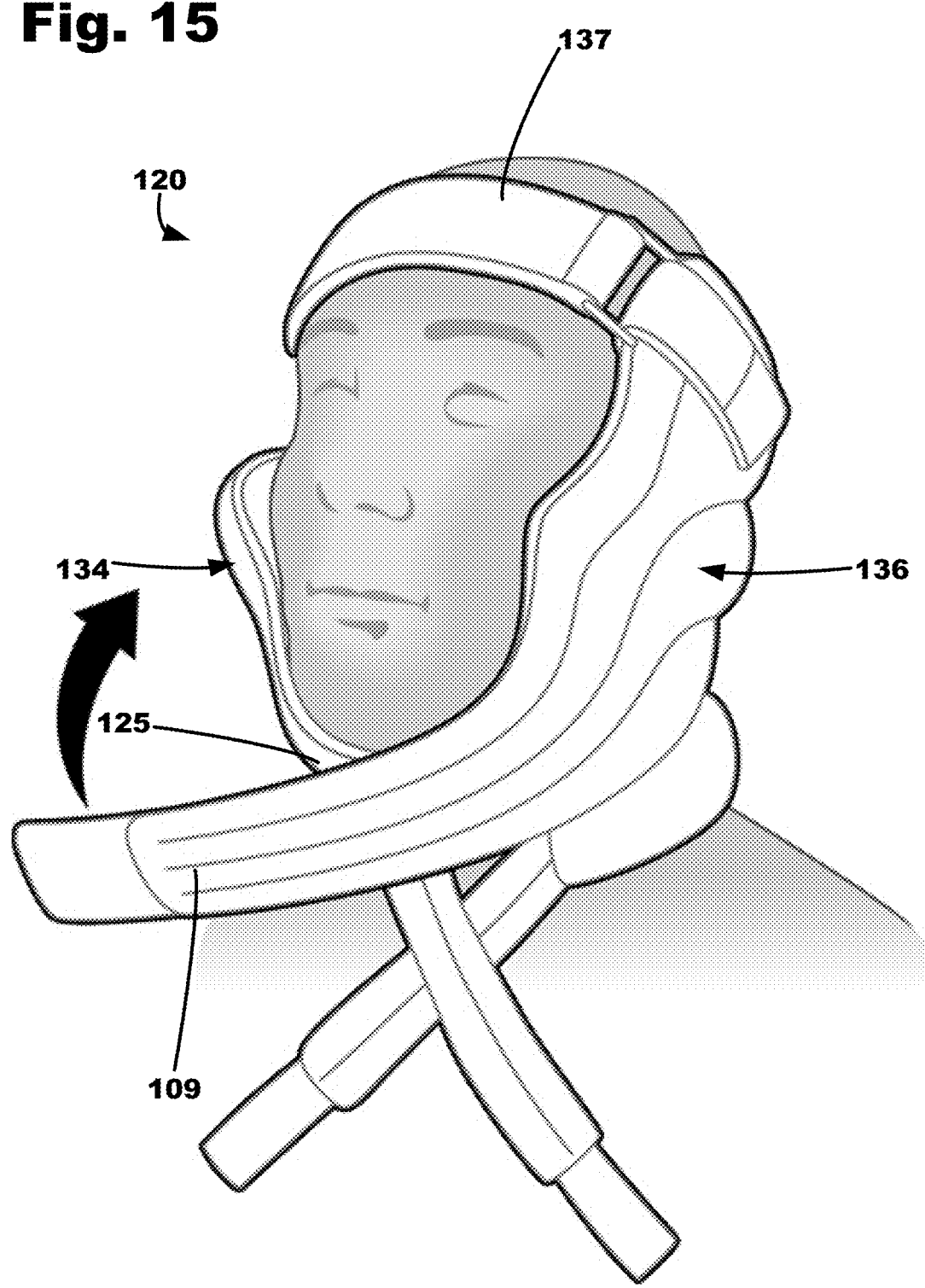
FIG. 15 is a front perspective view of the head garment portion of FIG. 5A being further coupled about the chin of the head.

Donning the head garment portion 120 is depicted in FIGS. 13-16. The head garment portion 120 may be wrapped around a head as shown in FIG. 13 and the forehead strap 137 may be tightened and secured (e.g., coupled using hook-and-loop fasteners, a buckle, etc.). Next, the under-chin garment portion of the head garment portion 120 may be secured underneath the patient's chin or mandible. More specifically, the right under-chin portion 125 may be moved underneath the chin or mandible as shown in FIG. 14, and then the left under-chin portion 109 may be moved underneath the chin or mandible as shown in FIG. 15 over the right under-chin portion 125. Next, the left under-chin portion 109 may be coupled to the right under-chin portion 125 and/or another portion of the right head garment portion 134 to secure the under-chin portion about the chin or mandible of the head.

In this embodiment, the under-chin garment portion including the left under-chin portion 109 and the under-chin portion 125 may be configured to be located between the neck of the body and the point, or end, of the chin or mandible of the user. In other words, the under-chin garment portion is not configured to extend past, beyond, or forward from the chin or mandible of the user. Additionally, the under-chin garment portion may also be configured so as to not interfere with the airway of the body proximate the laryngeal prominence ("Adam's apple") of the neck and/or to provide the open region 115 between the neck garment portion 110 and the torso garment portion 140. The general "U"-shape of the head garment portion 120 or the general "L"-shapes of the right, left head garment portions 134, 136 may provide such functionality and usability (e.g., not interfering with the neck's airway or laryngeal prominence). In one or more embodiments, the under-chin garment portion may not include all of the plurality of pressure applying regions 121 of the head garment portion 120. In other words, the under-chin garment portion may include less than all of the plurality of pressure applying regions 121 of the head garment portion 120. For example, in at least one embodiment, the under-chin garment portion may include two of the four pressure applying regions of the head garment portion 120.

Figure 16:
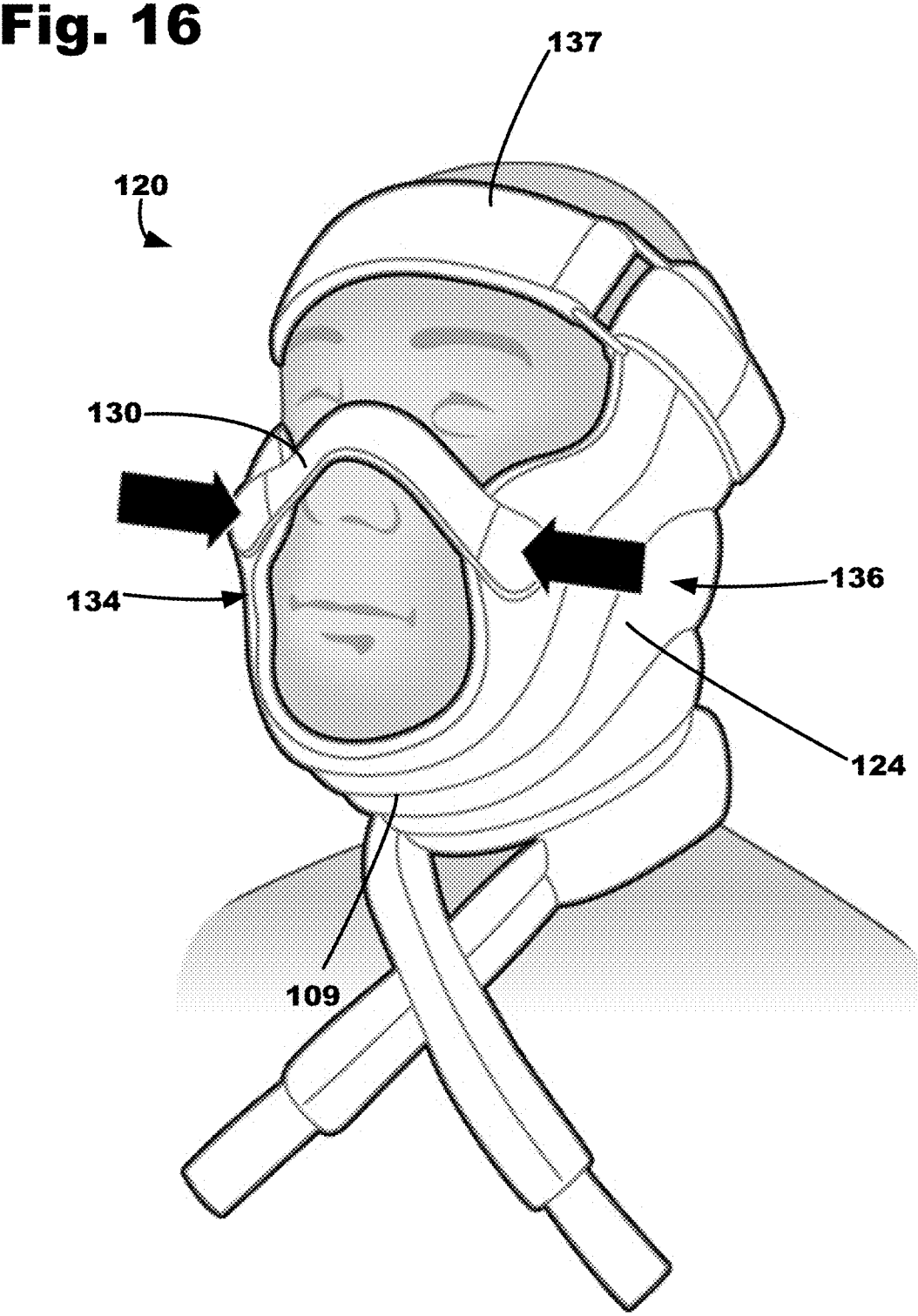
FIG. 16 is a front perspective view of the head garment portion of FIG. 5A being coupled about the nose of the head using a nose garment portion.

The head garment portion 120 may then be further fastened or secured with a nose portion 130 as shown in FIG. 16. The nose portion 130 may extend between and be coupled to the right head garment portion 134 and the left head garment portion 136 to, e.g., provide support between the right head garment portion 134 and the left head garment portion 136, assist in locating each of the right and left cheek garment portions 122, 124 adjacent the right and left cheeks of the head so as to be configured to apply pressure, etc. The nose portion 130 may be fixedly coupled to the head garment 120 such as, e.g., shown in the plan view of FIG. 6. More specifically, the nose portion 130 may be fixedly coupled, or integral with, the left head garment portion 136, and then, upon donning the head garment 120, the nose portion 130 may be removably coupled, or attached, to the right head garment portion 134 (e.g., using hook-and-loop fasteners). In other embodiments, the nose portion 130 may be separate piece from the head garment 120, and may be removably coupled (e.g., using hook-and-loop fasteners) to both the left and right head garment portions 136, 134 after donning the head garment 120. Further, in one or more embodiments, additional non-pressure applying (e.g. non-inflatable) strapping 198 may be provided for use in further securing the head and/or neck garment portions 120, 110 as shown in FIGS. 13-16.

As described herein, the exemplary compression garments and portions thereof may be configured move lymph from the head downward to the torso. To do so, the exemplary compression garments and portions thereof include a plurality of pressure applying regions (e.g., defined by fluid chambers, etc.) that may be configured to apply pressure in exemplary sequences and time intervals. A few exemplary embodiments of the sequences of chambers are described herein with respect to FIGS. 18-19.

Figure 18:
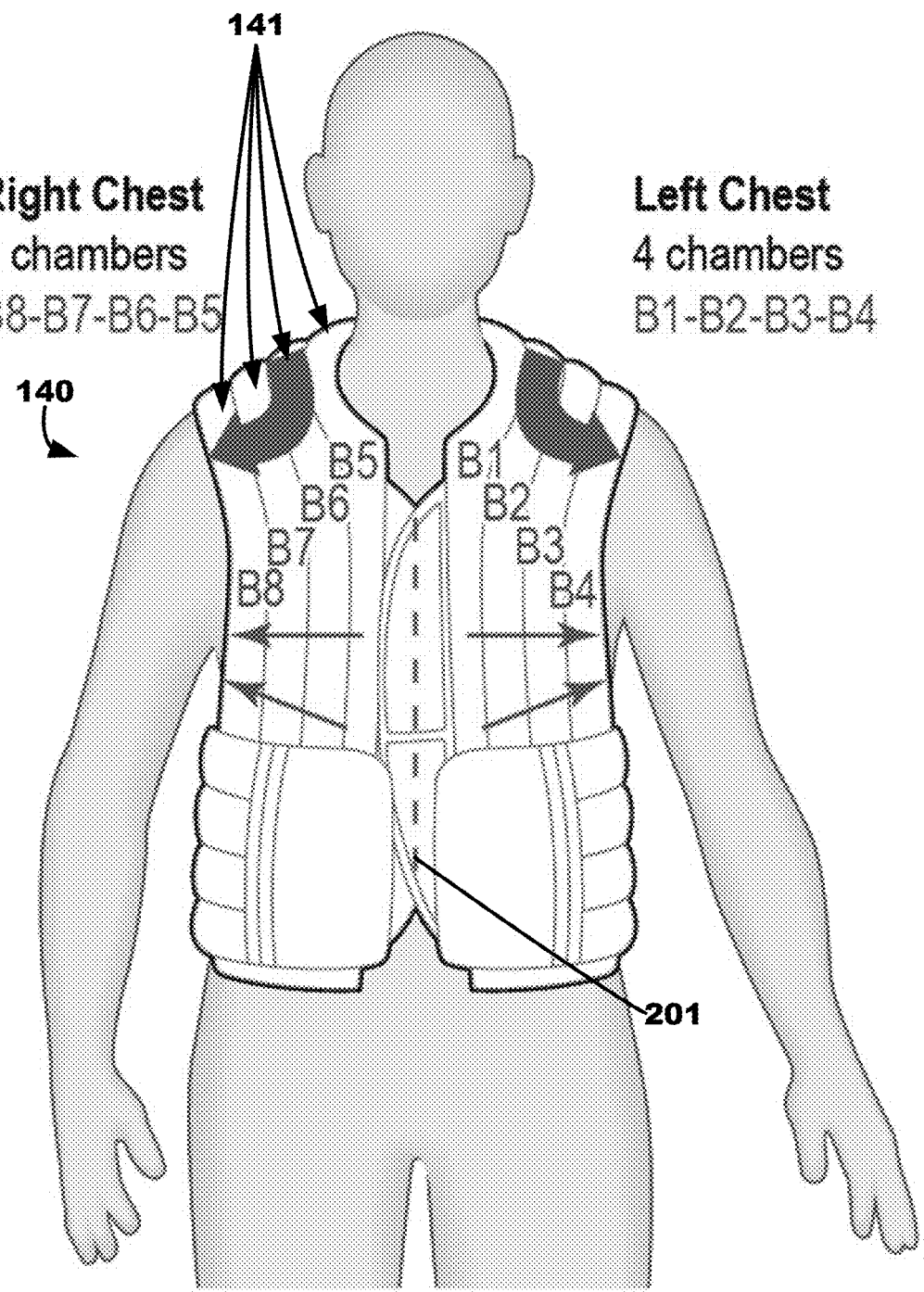
FIG. 18 is a front view of the torso garment portion of FIG. 5A located on a body further illustrating an exemplary torso pressure application sequence.

An exemplary torso garment portion 140 donned on a body 10 is depicted in FIG. 18. In this embodiment, the left and right torso garment portions 151, 152 are not attached using a zipper but instead using overlap portions. As shown, the pressure applying regions 141 are labeled B1, B2, B3, B4, B5, B6, B7, & B8 similar to as shown in FIG. 5A. Each of the pressure applying regions 141 may apply many different levels or values of pressure to the regions of the torso which correspond to or are adjacent (upon donning) thereto. For example, when the torso garment portion 140 is configured to use, or include, fluid fillable chambers for each of the pressure applying regions 141, the levels or values of pressure may be described in terms of millimeters of Mercury (mmHg). However, it is to be understood that the actual pressure applied to the torso of the body is not just dependent on the pressure applied by the pressure applying regions 141 (e.g., the fluid chambers) but is also dependent on how "tightly" the torso garment portion 140 is wrapped and coupled about the torso. Generally, users are instructed to wrap the torso garment portion 140 about their torso to provide a "snug" fit.

The pressure applying regions 141 of the torso garment portion 140 can be described as either providing a normal, or first, pressure value or providing an increased, or second, pressure value (e.g., the increased, or second, pressure value being greater than the normal, or first, pressure value). In at least one embodiment, the first, or normal, pressure value for the pressure applying regions 141 of the torso garment portion 140 is about 0 mmHG, about 10 mmHG, about 20 mmHG, about 30 mmHG, about 50 mmHG, about 60 mmHG, etc. (over atmospheric pressure) and the second, or increased, pressure value for the pressure applying regions 141 of the torso garment portion 140 is about 30 mmHG, about 40 mmHG, about 45 mmHG, about 50 mmHG, about 70 mmHg, about 100 mmHG, etc. (over atmospheric pressure). For example, the first, or normal, pressure value for the pressure applying regions 141 of the torso garment portion 140 may be greater than or equal to about 0 mmHg, greater than or equal to about 5 mmHg, about 10 mmHg, greater than or equal to about 20 mmHg, greater than or equal to about 30 mmHg, greater than or equal to about 40 mmHg, greater than or equal to about 50 mmHg, greater than or equal to about 60 mmHg, etc. Further, for example, the first, or normal, pressure value for the pressure applying regions 141 of the torso garment portion 140 may be less than or equal to about 80 mmHg, less than or equal to about 70 mmHg, less than or equal to about 55 mmHg, less than or equal to about 45 mmHg, less than or equal to about 35 mmHg, etc. For example, the second, or increased, pressure value for the pressure applying regions 141 of the torso garment portion 140 may be greater than or equal to about 20 mmHg, greater than or equal to about 40 mmHg, greater than or equal to about 50 mmHg, greater than or equal to about 60 mmHg, greater than or equal to about 70 mmHg, greater than or equal to about 80 mmHg, greater than or equal to about 90 mmHg, greater than or equal to about 105 mmHg, greater than or equal to about 120 mmHg, greater than or equal to about 140 mmHg, greater than or equal to about 160 mmHg, greater than or equal to about 190 mmHg, etc. For example, the second, or increased, pressure value for the pressure applying regions 141 of the torso garment portion 140 may be less than or equal to about 300 mmHg, less than or equal to about 250 mmHg, less than or equal to about 200 mmHg, less than or equal to about 175 mmHg, less than or equal to about 150 mmHg, less than or equal to about 130 mmHg, less than or equal to about 110 mmHg, less than or equal to about 100 mmHg, less than or equal to about 95 mmHg, less than or equal to about 85 mmHg, less than or equal to about 75 mmHg, less than or equal to about 65 mmHg, less than or equal to about 45 mmHg, less than or equal to about 30 mmHg, etc.

As shown in FIG. 18, the pressure applying regions 141 of the torso garment portion 140 may apply pressure in an "inward-to-outward" sequence from the central axis of the body 10. For example, each of the pressure applying regions 141 (B1, B2, B3, B4, B5, B6, B7, & B8) may be configured to apply the first pressure value, and then pressure applying regions B1 & B5, which are the closest pressure applying regions 141 to the axis 201, may apply the second pressure value for a selected period of time such as, e.g., about 0.2 seconds to about 4.0 seconds. It is be understood that the air may be introduced into a chamber defining the respective pressure applying region from a pump for the selected timed period. When a chamber, and thus pressure applying region, is not receiving air during the selected time period, the chamber may be vented to, or bled off to, the atmosphere through a valve. Additionally, it is to be understood that when the selected time period expires, the sequence may immediately move to the next pressure applying region. Further, it is to be understood that some chambers corresponding to pressure applying regions may be bigger than others, and thus, the selected time period may be greater for larger chambers and less for smaller chambers to achieve the same pressure. The selected period of time for a pressure applying regions 141 to be configured at the second, or increased, pressure value may be greater than or equal to about 0.1 seconds, greater than or equal to about 0.2 seconds, greater than or equal to about 0.3 seconds, greater than or equal to about 0.4 seconds, greater than or equal to about 0.5 seconds, greater than or equal to about 0.7 seconds, etc. greater than or equal to about 1.0 seconds, etc., greater than or equal to about 1.2 seconds, etc., greater than or equal to about 1.5 seconds, etc., greater than or equal to about 1.9 seconds, etc., greater than or equal to about 2.4 seconds, etc. Further, for example, the selected period of time for a pressure applying regions 141 to be configured at the second, or increased, pressure value may be less than or equal to about 5.0 seconds, less than or equal to about 4.5 seconds, less than or equal to about 4.0 seconds, less than or equal to about 3.5 seconds, less than or equal to about 3.0 seconds, less than or equal to about 2.7 seconds, less than or equal to about 2.5 seconds, less than or equal to about 2.3 seconds, less than or equal to about 2.0 seconds, less than or equal to about 1.8 seconds, less than or equal to about 1.4 seconds, less than or equal to about 1.1 seconds, less than or equal to about 0.6 seconds, etc.

After expiration of the selected time period, the pressure applying regions B1 & B5 may be returned to applying the first pressure value and the pressure applying regions B2 & B6, which are the second closest pressure applying regions 141 to the axis 201, may be apply the second pressure value for a selected period of time. After expiration of the selected time period, the pressure applying regions B2 & B6 may be returned to applying the first pressure value and the pressure applying regions B3 & B7, which are the third closest pressure applying regions 141 to the axis 201, may be apply the second pressure value for a selected period of time, and subsequently, the same may occur for the last set of pressure applying regions B4 & B8.

Although in this embodiment, a pair of pressure applying regions 141 from the left and right torso garment portions are applying the same pressure values at the same times, in other embodiments, the pressure applying regions 141 from the right and left torso garment portions may be configured, or behave, differently. Further, in this embodiment, it may be described that pressure applying regions B1 & B5 are operably coupled B2 & B6 are operably coupled, B3 & B7 are operably coupled, and B4 & B8 are operably coupled (e.g., each of these pressure applying regions are described as being operably coupled such that they share the same or similar pressures, such that they are fluidly coupled, through tubes and valves for fluid flow).

Figure 19:
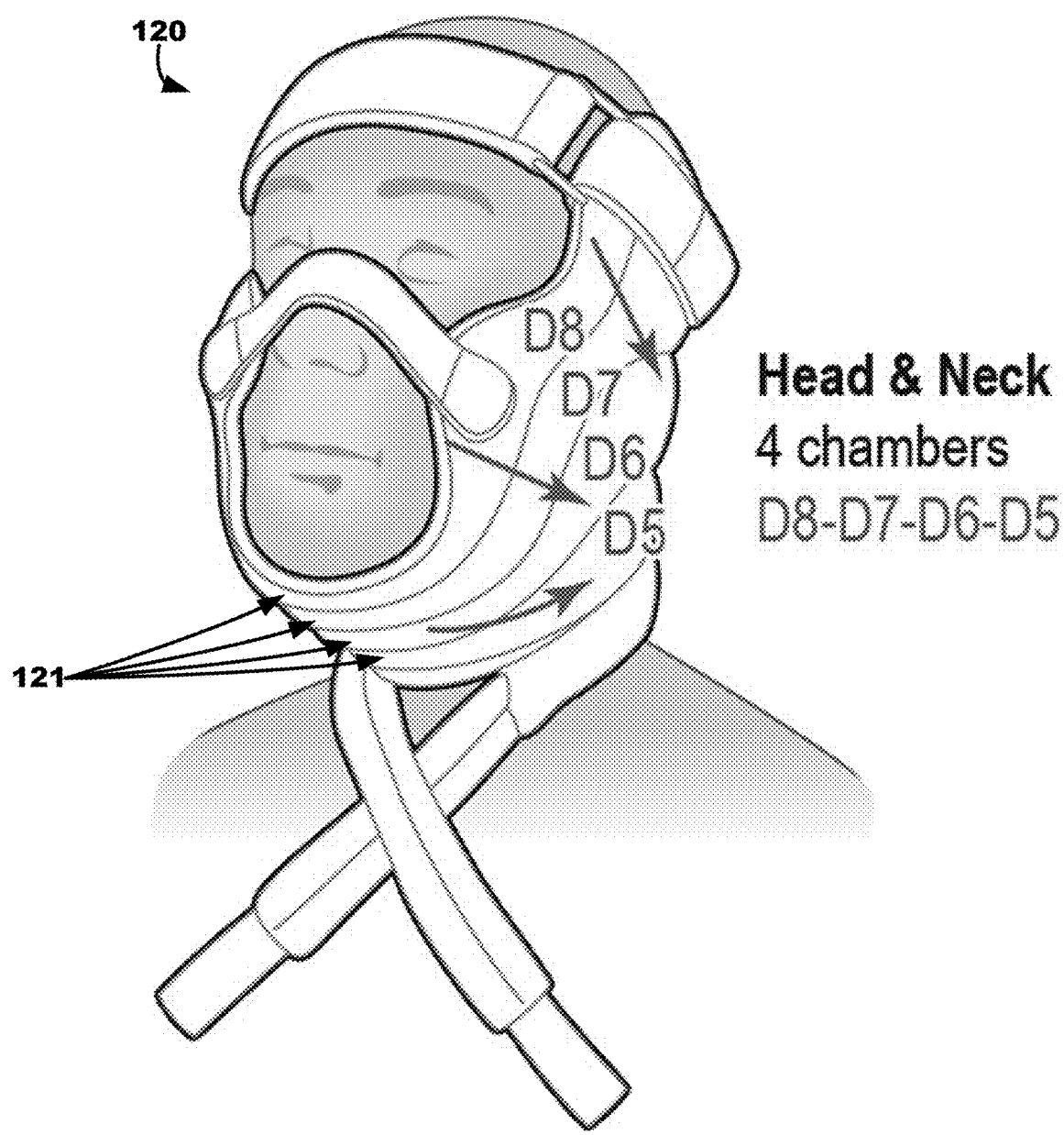
FIG. 19 is a front perspective view of the head garment portion of FIG. 6 located on a head further illustrating an exemplary head pressure application sequence.

The pressure applying regions 121 of the head garment portion 120 may operate in a similar manner as shown in FIG. 19. As shown, the pressure applying regions 121 of the head garment portion 120 may apply pressure in a "face-to-neck-and-downward" sequence. For example, each of the pressure applying regions 121 (D8, D7, D6, D5) may be configured to apply the first pressure value, and then pressure applying region D8, which is the closest pressure applying region 121 to the face of the head (e.g., closest to the nose of the head along the surface of the face), may be apply the second pressure value for a selected period of time such as, e.g., about 0.5 seconds about 3.0 seconds. The selected period of time for a pressure applying regions 121 to be configured at the second, or increased, pressure value may be greater than or equal to about 0.1 seconds, greater than or equal to about 0.2 seconds, greater than or equal to about 0.3 seconds, greater than or equal to about 0.4 seconds, greater than or equal to about 0.5 seconds, greater than or equal to about 0.7 seconds, etc. greater than or equal to about 1.0 seconds, etc., greater than or equal to about 1.2 seconds, etc., greater than or equal to about 1.5 seconds, etc., greater than or equal to about 1.9 seconds, greater than or equal to about 2.4 seconds, etc. Further, for example, the selected period of time for a pressure applying regions 121 to be configured at the second, or increased, pressure value may be less than or equal to about 5.0 seconds, less than or equal to about 4.5 seconds, less than or equal to about 4.0 seconds, less than or equal to about 3.5 seconds, less than or equal to about 3.0 seconds, less than or equal to about 2.7 seconds, less than or equal to about 2.5 seconds, less than or equal to about 2.3 seconds, less than or equal to about 2.0 seconds, less than or equal to about 1.8 seconds, less than or equal to about 1.4 seconds, less than or equal to about 1.1 seconds, less than or equal to about 0.6 seconds, etc.

After expiration of the selected time period, the pressure applying region D8 may be returned to applying the first pressure value and the pressure applying region D7, which is the second closest pressure applying region 121 to the face of the head, may be apply the second pressure value for a selected period of time. After expiration of the selected time period, the pressure applying region D7 may be returned to applying the first pressure value and the pressure applying region D6, which is the third closest pressure applying region 121 to the face of the head, may be apply the second pressure value for a selected period of time, and subsequently, the same may occur for the last pressure applying region D5.

The pressure application sequences depicted and described with respect to FIGS. 18-19 are only one example, and others may be used with the exemplary systems and apparatus described herein. Additionally, each of these pressure applying sequences may be repeated, used in conjunction with one another (either simultaneously or in succession), used with other sequences, and/or used with other compression garments. An exemplary method of therapy that may be implemented using one of the exemplary compression systems and garment portions of FIGS. 1 and 5-19 is depicted in FIGS. 20-22, which may use one or more of the pressure application sequences described with respect to FIGS. 18-19.

Figure 20:
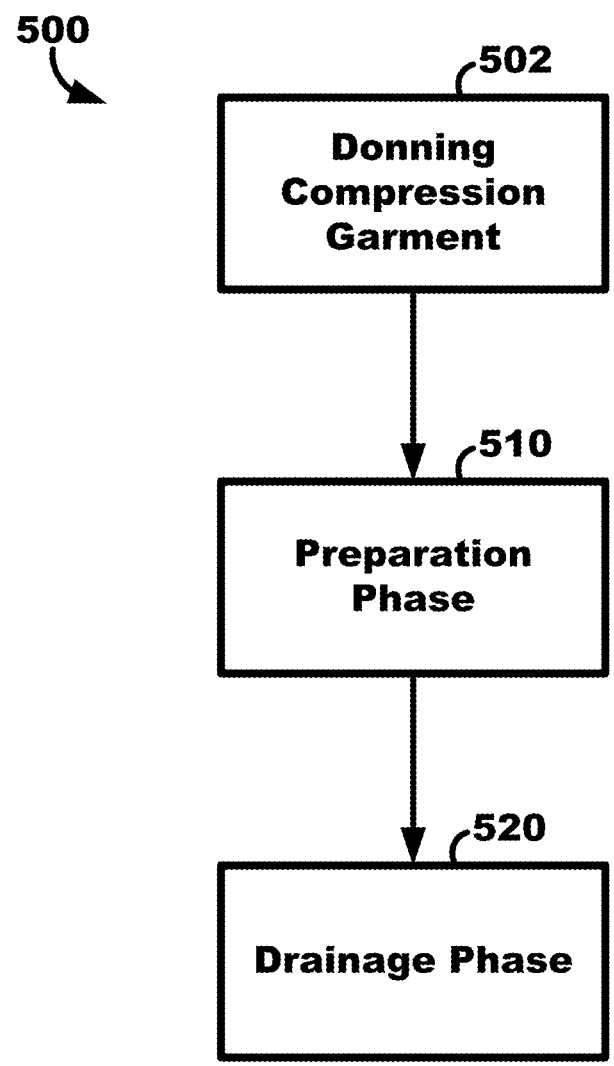
FIG. 20 is a block diagram of an exemplary method of therapy that may be implemented using the exemplary compression systems and garment portions of FIGS. 1 and 5-19.

The exemplary method 500 of FIG. 20 includes donning a compression garment 502 such as the exemplary torso garment portion 140 as shown in FIGS. 7-12 and the exemplary head garment portion 120 as shown in FIGS. 13-16. Once the compression garment has been donned 502, the exemplary method 500 may begin a preparation phase 510. The preparation phase 510 may be generally described as preparing a chest area for lymph to be drained from the neck and head regions (e.g., preparing axillary lymph nodes for drainage thereto, preparing the pathways for passage of lymph therethrough, etc.). The preparation phase 510 may include sequential and non-sequential sequences of increased pressured applied through to pressure applying regions from closest to the face of the head (e.g., the nose of the head across the surface of the face) to the neck and outward from a central axis endings through the body. Sequential sequences of increased pressured applied may be defined increasing the pressure in the pressure applying region closest to a location, then the next chamber closest, then the next chamber closest, and so on. Non-sequential sequences of increased pressured applied may be defined as any sequence of increasing the pressure that is not sequential. Further, some non-sequential sequences may include increasing the pressure applied in every other pressure applying region from the pressure applying region closest to a location outwardly, and then returning to the skipped pressure applying regions to apply increased pressure one at a time (e.g., "hand over hand" sequencing). Further, in some embodiments, each of the pressure applying regions may be increased in pressure quickly and then decreased quickly for a selected number of cycles or repeats.

As used herein, a pressure application sequence will be listed by a string of pressure applying regions, and the string of pressure applying regions will be listed in successive order of the pressure applying regions configured into the second, or increased, pressure value for a selected time period. For example, the first pressure applying region(s) in the list will be the first pressure applying region(s) to be configured in the second pressure value for the selected time period, the second pressure applying region(s) in the list will be the second pressure applying region(s) to be configured in the second pressure value for the next selected time period, and so on.

Figure 21:
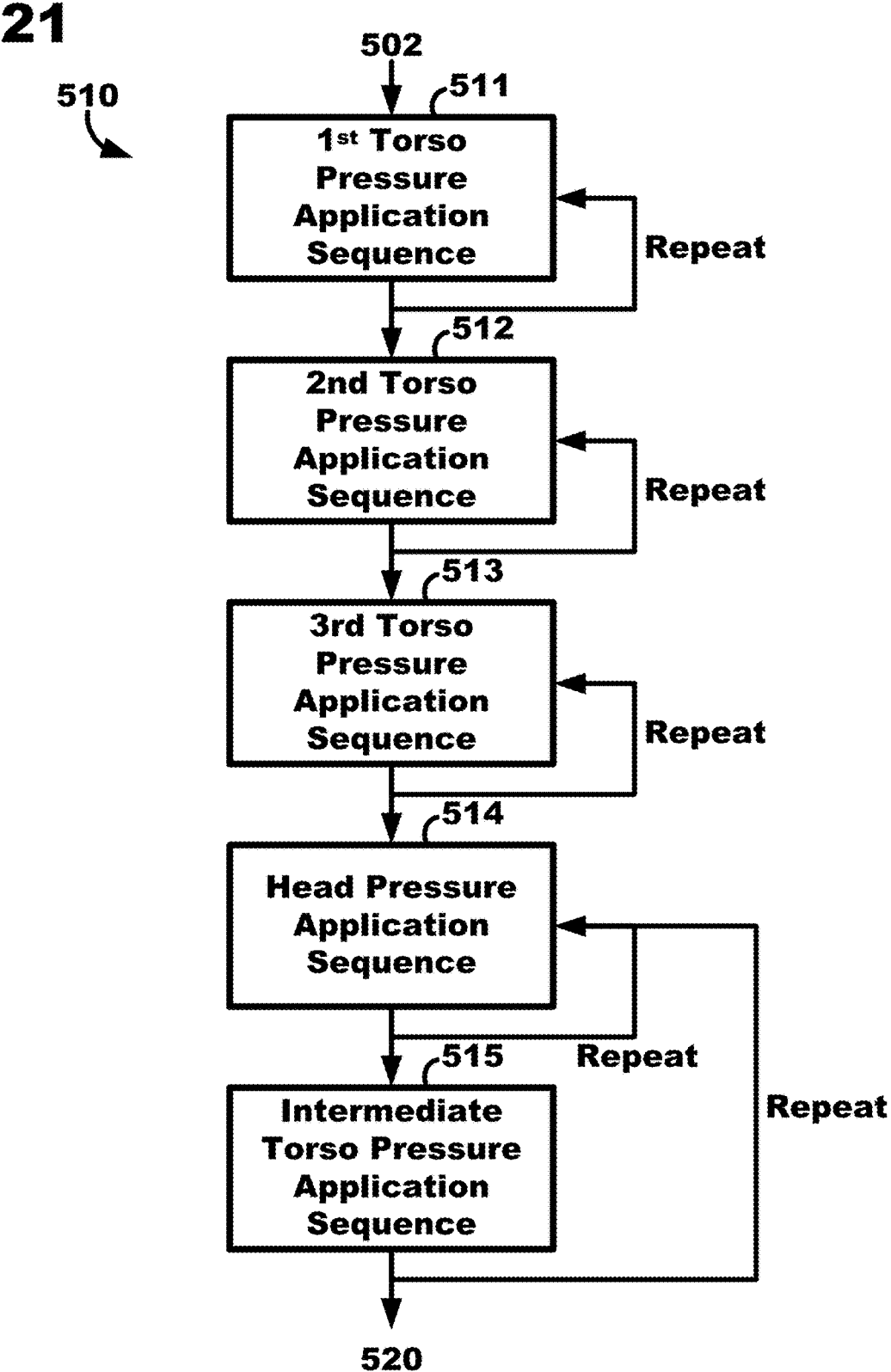
FIG. 21 is a block diagram of an exemplary preparation phase of the method of FIG. 20.
Figure 22:
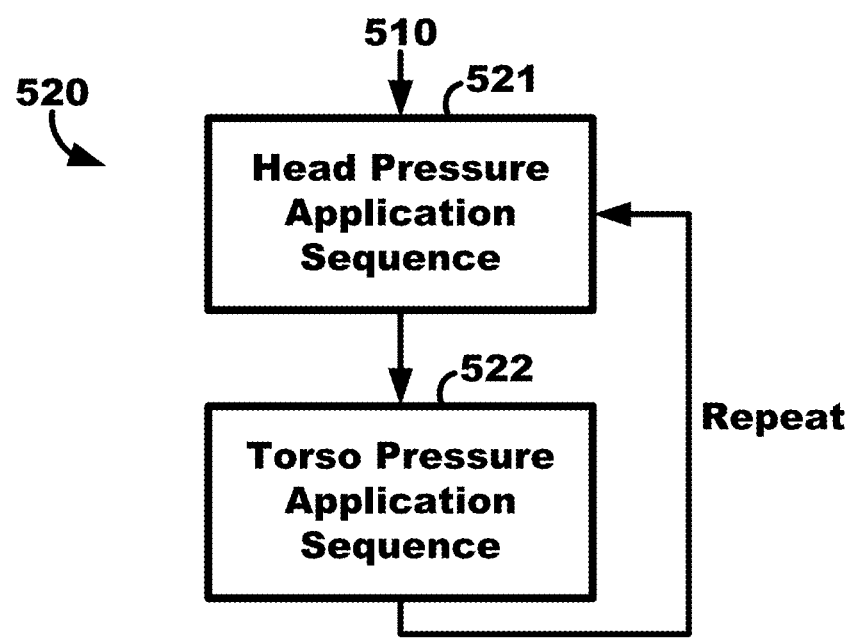
FIG. 22 is a block diagram of an exemplary drainage phase of the method of FIG. 20.

An exemplary preparation phase 510 is depicted in FIG. 21 and includes performing a first torso pressure application sequence 511 such as, e.g., B1 & B5, then B2 & B6, then B3 & B7, and then B4 & B8. The first torso pressure application sequence 511 may be described as being a sequential sequence. After the first torso pressure application sequence 511 has been performed once, it may be repeated as indicated by the arrow returning to box 511, or the method 510 may move on to the 2nd torso pressure application sequence 512. In this example, the first torso pressure application sequence 511 may be repeated as indicated by the "Repeat" label. For example, the first torso pressure application sequence 511 or other torso pressure application sequences may be repeated greater than once, greater than or equal to two times, greater than or equal to three times, greater than or equal to four times, greater than or equal to ten times, greater than or equal to fifteen times, greater than or equal to twenty times, greater than or equal to thirty times, greater than or equal to forty times, greater than or equal to fifty times, greater than or equal to seventy-five times, etc. Further, in other embodiments, the first torso pressure application sequence 511 or other torso pressure application sequences may be repeated less than or equal to two-hundred times, less than or equal to one-hundred fifty times, less than or equal to one-hundred times, less than or equal to ninety times, less than or equal to eighty times, less than or equal to seventy times, less than or equal to sixty times, less than or equal to forty-five times, less than or equal to thirty-five times, less than or equal to twenty-five times, less than or equal to fourteen times, less than five times, less than four times, less than three times, less than two times, etc.

After the first torso pressure application sequence 511 is repeated a selected number of times, the exemplary method may perform the second torso pressure application sequence 512 such as, e.g., B1 & B5, then B3 & B7, then B2 & B6, and then B4 & B8, which may also be repeated two times, three times, five times, ten times, twenty times, thirty times, fifty times, etc. and then the third torso pressure application sequence 513 such as, e.g., B1 & B5, then B2 & B6, then B3 & B7, and then B4 & B8, which may also be repeated two times, three times, five times, ten times, twenty times, thirty times, fifty times, etc. The second torso pressure application sequence 512 may be described as being a non-sequential sequence (e.g., every other and then return to skipped, "hand over hand," etc.) and the third torso pressure application sequence 513 may be described as being a sequential sequence.

After the third torso pressure application sequence 513, the exemplary method 500 may perform a head pressure application sequence 514 such as, e.g., D8, D7, D6, D5. After the head pressure application sequence 514 has been performed once, it may be repeated as indicated by the arrow returning to box 514, or the method 510 may move to the intermediate torso pressure application sequence 515. In this example, the head pressure application sequence 514 may be repeated as indicated by the "Repeat" label. For example, the head pressure application sequence may be repeated greater than once, greater than or equal to two times, greater than or equal to three times, greater than or equal to four times, greater than or equal to ten times, greater than or equal to fifteen times, greater than or equal to twenty times, greater than or equal to thirty times, greater than or equal to forty times, greater than or equal to fifty times, greater than or equal to seventy-five times, greater than or equal to hundred and ten times, greater than or equal to hundred and twenty times, etc. Further, in other embodiments, the head pressure application sequence may be repeated less than or equal to two-hundred times, less than or equal to one-hundred fifty times, less than or equal to one-hundred times, less than or equal to ninety times, less than or equal to eighty times, less than or equal to seventy times, less than or equal to sixty times, less than or equal to forty-five times, less than or equal to thirty-five times, less than or equal to twenty-five times, less than or equal to twenty-five times, less than fifteen times, less than or equal to twelve times, less than ten times, less than five times, etc.

After the head pressure application sequence 514 is repeated a selected number of times, the exemplary method 510 may perform an intermediate torso pressure application sequence 515 once such as, e.g., B1 & B5, then B2 & B6, then B3 & B7, and then B4 & B8 and return to the head pressure application sequence 514. Then, after the intermediate torso pressure application sequence 515 has been performed once, the head pressure application sequence 514 may be repeated, e.g., ten times, fifteen times, twenty-four times, thirty times, fifty times, etc., and afterwards, the intermediate torso pressure application sequence 515 may be performed once, twice, five times, ten times, twenty times, etc. Further, the head pressure application sequence 514 may be then repeated, e.g., ten times, fifteen times, twenty-four times, thirty times, fifty times, etc., and afterwards, the intermediate torso pressure application sequence 515 may be performed once, twice, five times, ten times, twenty times, etc.

After the intermediate torso pressure application sequence 515 is performed a third time, the preparation phase 510 may be complete, and the method 500 may move to the drainage phase 520. The drainage phase 520 may be generally described as applying pressure to the one or more pressure applying regions to move lymph from the head and neck towards and through the torso. In one or more embodiments, the drainage phase 520 may be described as a sequential application of pressure starting at the face of the head of the body extending to the neck of the body and outwardly from the axis of the body towards the sides of the body. In one or more embodiments, the drainage phase 520 may not be sequential but still configured to move lymph as described herein. The exemplary drainage phase method 520 as shown in FIG. 22 includes two sequences that may be repeated. More specifically, the drainage phase method 520 performs a head pressure application sequence 521 such as, e.g., such as, e.g., D8, then D7, then D6, then D5, then performs a torso pressure application sequence 522 such as, e.g., B1 & B5, then B2 & B6, then B3 & B7, and then B4 & B8, after performing the head pressure application sequence 521, and then repeats these successive sequences 521, 522 twice, five times, ten times, twenty times, twenty-five times, thirty times, forty times, fifty times, sixty times, seventy-five times, one hundred times, etc.

Further, for example, the head pressure application and torso pressure application sequences 521, 522 may be repeated greater than or equal to three times, greater than or equal to five times, greater than or equal to ten times, greater than or equal to fifteen times, greater than or equal to twenty times, greater than or equal to thirty times, greater than or equal to forty times, greater than or equal to fifty times, greater than or equal to seventy-five times, etc. Still further, for example, the head pressure application and torso pressure application sequences 521, 522 may be repeated less than or equal to two-hundred times, less than or equal to one-hundred fifty times, less than or equal to one-hundred times, less than or equal to ninety times, less than or equal to eighty times, less than or equal to seventy times, less than or equal to sixty times, less than or equal to forty-five times, less than or equal to thirty-five times, less than or equal to twenty-five times, less than or equal to fourteen times, less than or equal to nine times, less than or equal to six times, etc.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. A compression garment system comprising:
   a head and torso garment comprising:
   a plurality of head pressure applying regions controllable to apply pressure to a plurality of portions of a head of a body, wherein the plurality of head pressure applying regions are positioned in a concentric pattern radiating away from a face of the head of the body to apply pressure to the plurality of portions of the head of the body to move lymph from portions of the head proximate the face to a neck of the body, and
   a plurality of torso pressure applying regions controllable to apply pressure to a plurality of portions of a torso of the body; and
   a controller operably coupled to the head and torso garment to control pressure applied by the plurality of head pressure applying regions and the plurality of torso pressure applying regions in at least a preparation phase and a drainage phase,
   wherein, when in the preparation phase, the controller is configured to apply pressure to the plurality of portions of the torso and the plurality of portions of the head using the plurality of torso pressure applying regions and the plurality of head pressure applying regions to prepare the torso of the body for lymph to be drained from the head the neck of the body,
   wherein, when in the drainage phase, the controller is configured to apply pressure to the plurality of portions of the torso and the plurality of portions of the head using the plurality of torso pressure applying regions and the plurality of head pressure applying regions to move lymph at least from the head to the neck to the torso.

2. The compression garment system of claim 1, wherein the body extends along an axis, and wherein, when in the preparation phase, the controller is further configured to:
   apply pressure to the plurality of portions of the torso of the body using a torso pressure application sequence using the plurality of torso pressure applying regions, wherein the torso pressure application sequence comprises application of increased pressure sequentially from the plurality of portions of the torso closest to the axis of the body to portions of the plurality of portions of the torso furthest away from the axis of the body.

3. The compression garment system of claim 1, wherein the body extends along an axis, and wherein, when in the preparation phase, the controller is further configured to:

apply pressure to the plurality of portions of the head of the body outwardly from the face of the head using to the plurality of head pressure applying regions after applying pressure to the plurality of torso pressure applying regions.

4. The compression garment system of claim 1, wherein the body extends along an axis, and wherein, when in the drainage phase, the controller is further configured to:
apply pressure to the plurality of portions of the head of the body outwardly from the face of the head using the plurality of head pressure applying regions; and
apply pressure to the plurality of portions of the torso of the body using the plurality of torso pressure applying regions using a torso pressure application sequence after applying pressure to the plurality of head pressure applying regions, wherein the torso pressure application sequence comprises application of increased pressure sequentially from the plurality of portions of the torso closest to the axis of the body to portions of the plurality of portions of the torso furthest away from the axis of the body.

5. The compression garment system of claim 1, wherein the body extends along an axis, wherein the controller is further configured to apply pressure to the plurality of portions of the torso using the plurality of torso pressure applying regions using a torso pressure application sequence, wherein the torso pressure application sequence comprises application of increased pressure sequentially from the plurality of portions of the torso closest to the axis of the body and to portions of the plurality of portions of the torso furthest away from the axis of the body.

6. The compression garment system of claim 1, wherein the body extends along an axis, wherein the controller is further configured to apply pressure to the plurality of portions of the torso using the plurality of torso pressure applying regions using a torso pressure application sequence, wherein the torso pressure application sequence comprises application of increased pressure non-sequentially from portions of the plurality of portions of the torso closest to the axis of the body to portions of the plurality of portions of the torso furthest away from the axis of the body.

7. The compression garment system of claim 1, wherein the controller is further configured to apply pressure to the plurality of portions of the head using the plurality of head pressure applying regions using a head pressure application sequence, wherein the head pressure application sequence comprises application of increased pressure sequentially to portions of the plurality of portions of the head closest to the face of the head to portions of the plurality of portions of the head further away from the face of the head and closest the neck of the body.

8. The compression garment system of claim 1, wherein the controller is further configured to apply pressure to the plurality of portions of the head using the plurality of head pressure applying regions using a head pressure application sequence, wherein the head pressure application sequence comprises application of increased pressure non-sequentially to portions of the plurality of portions of the head closest to the face of the head to portions of the plurality of portions of the head further away from the face of the head and closest the neck of the body.

9. The compression garment system of claim 1, wherein the controller is further configured to:
apply a first pressure to all but one of the plurality of portions of the head using the plurality of head pressure applying regions; and
apply a second pressure greater than the first pressure to one of the plurality of portions of the head using the plurality head pressure applying regions.

10. The compression garment system of claim 9, wherein the second pressure is greater than or equal to 20 mmHG.

11. The compression garment system of claim 1, wherein the controller is further configured to:
apply a first pressure to all but one of the plurality of portions of the torso using the plurality of torso pressure applying regions; and
apply a second pressure greater than the first pressure to one of the plurality of portions of the torso using the plurality torso pressure applying regions.

12. The compression garment system of claim 11, wherein the second pressure is greater than or equal to 40 mmHG.

13. The compression garment system of claim 1, wherein the head and torso garment comprises:
a plurality of head cells corresponding to the plurality of head pressure applying regions and configured to receive fluid to apply pressure to the plurality of portions of the head when the garment is donned, and
a plurality of torso cells corresponding to the plurality of torso pressure applying regions and configured to receive fluid to apply pressure to the plurality of portions of the torso when the garment is donned.

14. The compression garment system of claim 1, wherein the head and torso garment comprises:
a head garment portion comprising the plurality of head pressure applying regions;
a torso garment portion comprising the plurality of torso pressure applying regions; and
a neck garment portion coupled to torso garment portion comprising at least one neck pressure applying region controllable to apply pressure to at least one neck portion of the body during the preparation and drainage phases.

15. The compression garment system of claim 1, wherein the head and torso garment comprises a plurality of layers to define the plurality of head pressure applying regions and the plurality of torso pressure applying regions, wherein the plurality of layers comprise:
a fabric exterior facing layer; and
a first polymer layer and a second polymer layer defining a plurality of chambers, the plurality of chambers corresponding to and defining the plurality of head pressure applying regions and the plurality of torso pressure applying regions.

* * * * *

UNITED STATES PATENT AND TRADEMARK OFFICE
CERTIFICATE OF CORRECTION

| | | |
|---|---|---|
| PATENT NO. | : 11,154,452 B2 | Page 1 of 1 |
| APPLICATION NO. | : 15/411059 | |
| DATED | : October 26, 2021 | |
| INVENTOR(S) | : Daniel G. Chase et al. | |

It is certified that error appears in the above-identified patent and that said Letters Patent is hereby corrected as shown below:

On the Title Page

In the (56) References Cited, U.S. Patent Documents, Column 1, on page 2, add --D293,932 S 01/1988 Ramseyer--.

In the Claims

Claim 1 (Column 34, Line 46) 'from the head the neck' should read --from the head and the neck--.

Claim 11 (Column 36, Lines 21-22) 'using the plurality torso' should read --using the plurality of torso--.

Claim 14 (Column 36, Line 41) 'coupled to torso garment portion' should read --coupled to the torso garment portion--.

Signed and Sealed this
Thirteenth Day of September, 2022

Katherine Kelly Vidal
*Director of the United States Patent and Trademark Office*